(12) United States Patent
Hart et al.

(10) Patent No.: US 11,918,237 B2
(45) Date of Patent: Mar. 5, 2024

(54) SYSTEMS AND METHODS FOR ROBOTIC ANKLE ARTHROPLASTY

(71) Applicant: Orthosoft ULC, Montreal (CA)

(72) Inventors: Cornelius Hart, Montreal (CA); Jean-Francois Girouard, Terrasse-Vaudreuil (CA); Bahareh Khatibi, Montreal (CA); Jeremie Menard, Montreal (CA); Antony Bou-Francis, Verdun (CA)

(73) Assignee: Orthosoft ULC, Montreal (CA)

( * ) Notice: Subject to any disclaimer, the term of this patent is extended or adjusted under 35 U.S.C. 154(b) by 415 days.

(21) Appl. No.: 17/185,494

(22) Filed: Feb. 25, 2021

(65) Prior Publication Data

US 2021/0267611 A1 Sep. 2, 2021

Related U.S. Application Data

(60) Provisional application No. 62/984,033, filed on Mar. 2, 2020.

(51) Int. Cl.
*A61B 17/15* (2006.01)
*A61B 17/17* (2006.01)
(Continued)

(52) U.S. Cl.
CPC .......... *A61B 17/1775* (2016.11); *A61B 34/32* (2016.02); *A61F 2/4202* (2013.01);
(Continued)

(58) Field of Classification Search
CPC .............................. A61B 17/15–17/158; A61F 2/4202–2002/4223
See application file for complete search history.

(56) References Cited

U.S. PATENT DOCUMENTS 8,337,503 B2  12/2012  Lian
8,884,618 B2  11/2014  Mahfouz
(Continued)

FOREIGN PATENT DOCUMENTS

| EP | 1931275 A1 | 6/2008 |
|---|---|---|
| WO | 2007041094 | 4/2007 |
| WO | WO-2021174346 A1 | 9/2021 |

OTHER PUBLICATIONS

"European Application Serial No. 21764460.8, Response to Communication pursuant to Rules 161(2) and 162 EPC filed Apr. 20, 2023", 16 pgs.
(Continued)

*Primary Examiner* — Zade Coley
(74) *Attorney, Agent, or Firm* — SCHWEGMAN LUNDBERG & WOESSNER, P.A.

(57) ABSTRACT

Instrument systems for performing total ankle arthroplasties comprise an instrument adapter, a talus reaming guide and a talar trial system. The instrument adapter comprises a coupler for attaching to a robotic surgical arm, an extension arm extending from the coupler, a talus resection block attached to the extension arm, including a talus cutting guide surface, and an interface for receiving another instrument. The talus reaming guide comprises a second attachment member for coupling to the interface, and a reaming hoop for confining movement of a reamer. The talar trial system comprises a talar adapter for connecting to the interface, and a talar trial couplable to the talar adapter, the talar trial including a talar bearing surface. The talus resection block can serve as a universal instrument adapter for mounting the talus reaming guide, the talar trial system and a tibia resection block for performing a total ankle arthroplasty.

14 Claims, 18 Drawing Sheets

(51) Int. Cl.
*A61B 34/32* (2016.01)
*A61F 2/42* (2006.01)
*A61F 2/46* (2006.01)
*A61B 17/00* (2006.01)

(52) U.S. Cl.
CPC .. *A61F 2/4684* (2013.01); *A61B 2017/00477* (2013.01); *A61F 2002/4207* (2013.01)

(56) References Cited

U.S. PATENT DOCUMENTS

| | | | |
|---|---|---|---|
| 9,675,461 B2 | 6/2017 | Mahfouz | |
| 10,136,952 B2* | 11/2018 | Couture | A61B 5/4585 |
| 10,314,597 B2* | 6/2019 | Saltzman | A61B 17/1682 |
| 2009/0171371 A1 | 7/2009 | Nixon | |
| 2012/0130376 A1* | 5/2012 | Loring | A61F 2/4202 |
| | | | 606/90 |
| 2012/0271314 A1* | 10/2012 | Stemniski | A61B 17/1775 |
| | | | 606/87 |
| 2014/0188236 A1* | 7/2014 | McGinley | A61F 2/4684 |
| | | | 623/21.18 |
| 2016/0128701 A1* | 5/2016 | Neal | A61F 2/4202 |
| | | | 606/87 |
| 2016/0361071 A1 | 12/2016 | Mahfouz | |
| 2017/0296158 A1* | 10/2017 | Loring | A61B 17/1682 |
| 2017/0312035 A1 | 11/2017 | May et al. | |
| 2019/0240045 A1 | 8/2019 | Couture | |

OTHER PUBLICATIONS

"International Application Serial No. PCT/CA2021/050264, International Preliminary Report on Patentability dated Sep. 6, 2022", 5 pgs.

"International Application Serial No. PCT/CA2021/050264, International Search Report dated May 26, 2021", 15 pgs.

"International Application Serial No. PCT/CA2021/050264, Written Opinion dated May 26, 2021", 4 pgs.

"Australian Application Serial No. 2021229915, First Examination Report dated Oct. 23, 2023", 4 pgs.

"Canadian Application Serial No. 3,173,993, Examiners Rule 86(2) Report dated Nov. 2, 2023", 5 pgs.

* cited by examiner

SYSTEMS AND METHODS FOR ROBOTIC ANKLE ARTHROPLASTY

CLAIM OF PRIORITY

This application claims the benefit of U.S. Provisional Patent Application Ser. No. 62/984,033, filed on Mar. 2, 2020, the benefit of priority of which is claimed hereby, and which is incorporated by reference herein in its entirety.

TECHNICAL FIELD

The present disclosure is directed to devices and methods for use in performing ankle arthroplasty, such as total ankle replacement procedures.

BACKGROUND

Imaging of anatomical features can be useful in preparing for and performing surgical procedures. For example, patient-specific instruments can be derived from patient imaging and robotic surgical systems can be configured to track anatomy of a patient based on registration with patient imaging.

Patient-specific instruments have been successfully deployed for many surgical procedures. By creating three-dimensional (3D) models of anatomy of a patient from medical images, surgeries can be customized using virtual 3D surgical planning for specific patients.

In robotic surgical systems, the shape of the anatomy in the patient imaging can be registered with another frame of reference, such as the physical space of an operating room where the robotic surgical system is located. Robotic surgical arms can be used to hold various instruments in place in a desired orientation relative to both the anatomy and operating room during a procedure. As such, movements of the robotic arm can be used to illustrate movements of the instrument relative to the anatomy on the imaging of the patient.

Total ankle arthroplasties can be complicated procedures that utilize a plurality of different instruments that are switched during the procedure and result in the anatomy being repositioned throughout the procedure, thereby increase the time and cost of the procedure. U.S. Pat. No. 8,337,503 to Lian and Pub. No. US 2016/0361071 to Mahfouz describe cutting guides and instruments for use in total ankle replacement surgery.

OVERVIEW

The present inventors have recognized, among other things, that problems to be solved with traditional total ankle arthroplasties involve positioning of the ankle joint in alignment to receive a prosthetic device that engages the tibia bone and the talus bone. As such, the depth of the resections of the tibia bone and talus bone must be coordinated to ensure a gap height for proper seating of the prosthetic device. Maintaining gap height in conventional procedures can be difficult as different guides and instruments are moved into and out of the surgical site.

The present inventors have also recognized, among other things, that problems to be solved with traditional total ankle arthroplasties include the need for having to attach multiple instruments for properly resecting the tibia bone and the talus bone. Each of these instruments needs to be properly aligned with the ankle joint to, among other things, ensure proper gap height. Use of too many instruments can be off-putting for surgeons due to increased complexity and time of the surgeries. Furthermore, surgeries that require multiple instruments have conventionally been unsuitable for robot-assisted surgeries due to complexities of having to attach multiple instruments to the robotic surgical arm and the need to register each of these instruments individually.

The present subject matter can provide a solution to these and other problems, such as by providing an alignment boot that can simultaneously hold the tibia and talus bones of an ankle joint in alignment and secure the ankle joint to tracking elements for a robotic surgical system. Furthermore, the present subject matter can provide a solution to these and other problems, such as by providing a surgical instrument system that can include a universal instrument adapter that can be registered to the robotic surgical system and that can provide a platform for attaching multiple different instruments that can, via attachment to the universal instrument adapter, become registered to the robotic surgical system without the need for individually registering each attached instrument. An advantage of such a universal instrument adapter is the increased precision for the proper sizing and positioning of implants via a trial implant that can attach to the universal instrument adapter.

In an example, an instrument system for performing a total ankle arthroplasty can comprise an instrument adapter, a tibia resection block, a talus reaming guide and a talar trial system. The instrument adapter can comprise a coupler for attaching to a robotic surgical arm, an extension arm extending from the coupler, a talus resection block attached to the extension arm, the talus resection block including a talus cutting guide surface, and an interface for receiving another instrument. The tibia resection block can comprise a first attachment member for coupling to the interface, and a tibia cutting guide surface. The talus reaming guide can comprise a second attachment member for coupling to the interface, and a reaming hoop for confining movement of a reamer. The talar trial system can comprise a talar adapter for connecting to the interface, and a talar trial couplable to the talar adapter, the talar trial including a talar bearing surface.

In an additional example, a robotic surgical system can comprise a robotic arm configured to move an end of the robotic arm in relationship to a coordinate system for the surgical robot system, a universal instrument adapter comprising a coupler for attaching to the end of the robotic arm and an interface for receiving an attachment instrument, a set of attachment instruments wherein each attachment instrument having a geometry and being configured to couple with the interface, and a controller for the robotic surgical arm, the controller comprising a non-transitory storage medium having computer-readable instructions stored therein comprising dimensional data for the universal instrument adapter, dimensional data for the geometries of each of the attachment instruments, and instructions for moving the end of the robotic arm to position each of the attachment instruments into specific location within the coordinate system according to a surgical plan.

In another example, a method for performing a medical procedure using a robotic surgical arm can comprise attaching a universal instrument adapter to the robotic surgical arm, registering a position of the universal instrument adapter to a coordinate system of the robotic surgical arm, attaching a first attachment to the universal instrument adapter, moving the universal instrument adapter to a first location with the robotic surgical arm, performing a first step of the medical procedure with the first attachment, removing the first attachment from the universal instrument adapter, moving the universal instrument adapter to a second location with the robotic surgical arm, and performing a second step of the medical procedure with the universal instrument adapter.

DETAILED DESCRIPTION

Figure 1:
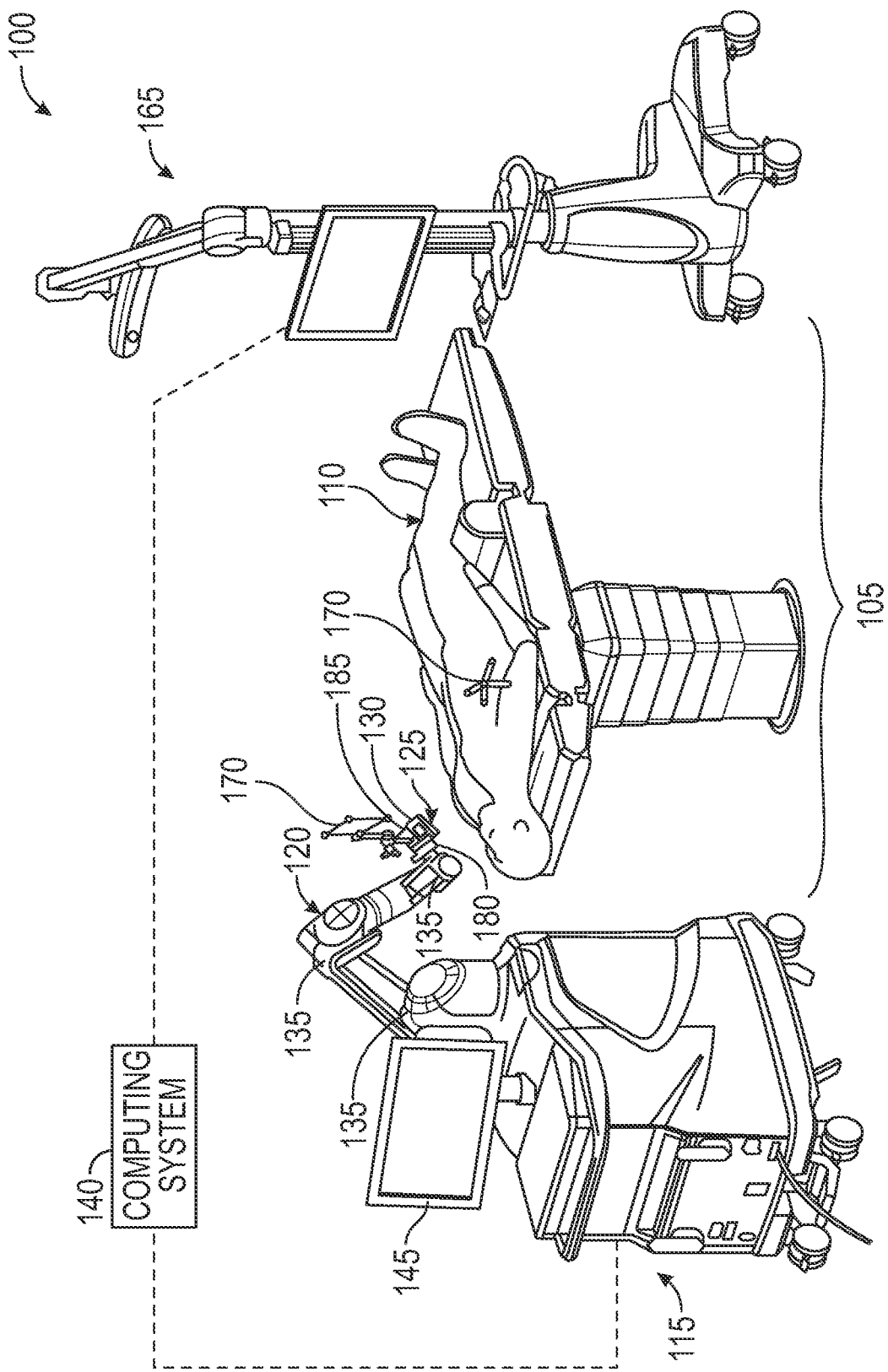
FIG. 1 is a diagrammatic view of an operating room including a robot-assisted surgical system comprising a robotic arm, a computing system and a tracking system.

FIG. 1 illustrates surgical system 100 for operation on surgical area 105 of patient 110 in accordance with at least one example of the present disclosure. Surgical area 105 in one example can include a joint and, in another example, can be a bone. Surgical area 105 can include any surgical area of patient 110, including but not limited to the shoulder, head, elbow, thumb, spine, and the like. Surgical system 100 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA® robot from Medtech, a Zimmer Biomet Holdings, Inc. company. In some examples, robotic arm 120 is cooperatively controlled with surgeon input on the end effector or surgical instrument, such as surgical instrument 125. In other examples, robotic arm 120 can operate autonomously. While not illustrated in FIG. 1, one or more positionable surgical support arms can be incorporated into surgical system 100 to assist in positioning and stabilizing instruments or anatomy during various procedures.

Figure 2:
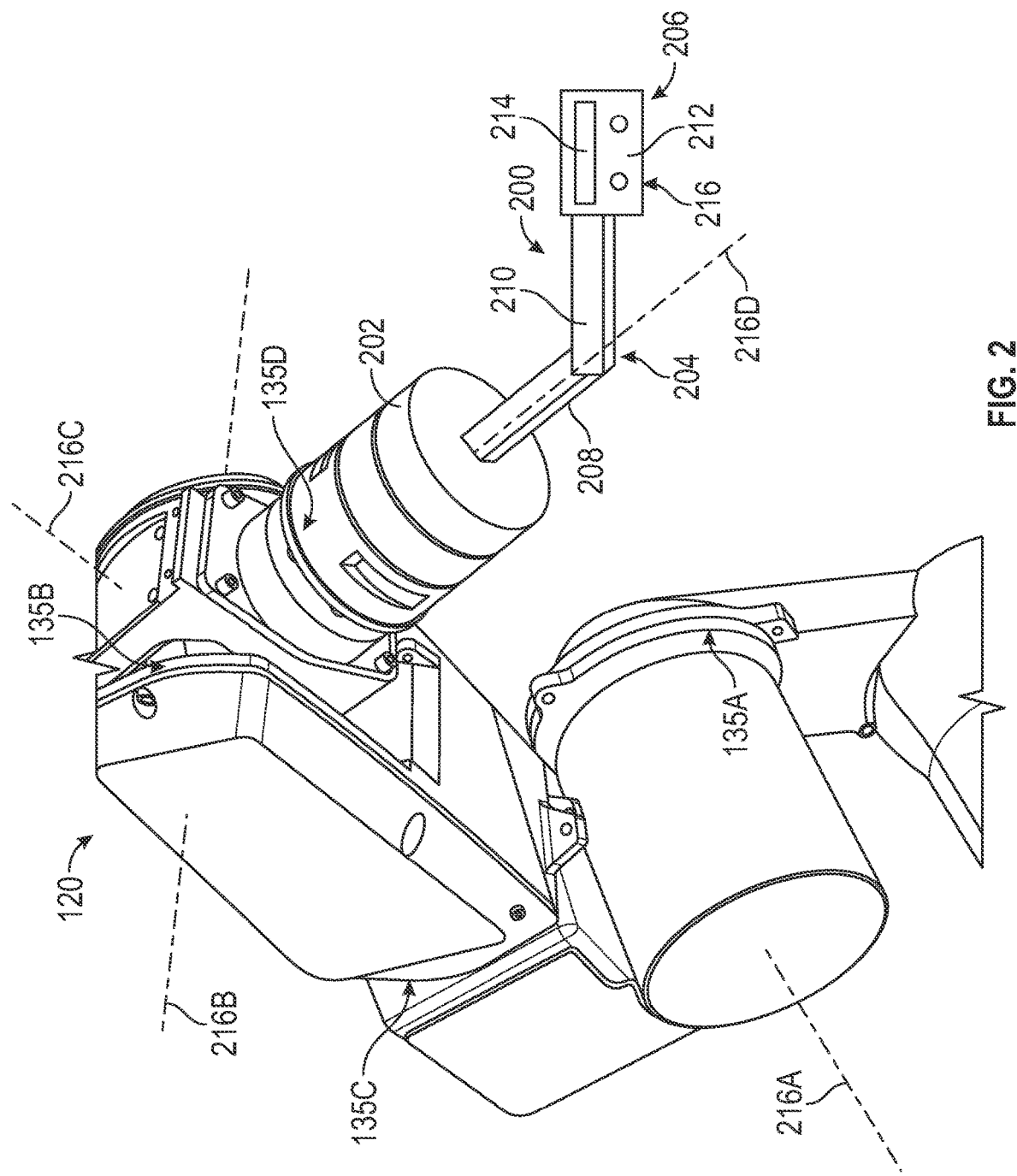
FIG. 2 is a schematic view of the robotic arm of FIG. 1 including a base instrument configured to provide cutting guide functions and serve as a platform for mounting components for additional surgical steps.

Each robotic arm 120 can rotate axially and radially and can receive a surgical instrument, or end effector, 125 at distal end 130. Surgical instrument 125 can be any surgical instrument adapted for use by the robotic system 115, including, for example, a guide tube, a holder device, a gripping device such as a pincer grip, a burring device, a reaming device, an impactor device such as a humeral head impactor, a pointer, a probe, an instrument guide, an instrument holder or a universal instrument adapter device as described herein or the like. Surgical instrument 125 can be positionable by robotic arm 120, which can include multiple robotic joints, such as joints 135, that allow surgical instrument 125 to be positioned at any desired location adjacent or within a given surgical area 105. As discussed below, robotic arm 120 can be used with surgical instrument system 300 of FIGS. 3A-3D to perform a total ankle arthroplasty using universal instrument adapter 200 (FIG. 2).

Robotic system 115 can also include computing system 140 that can operate robotic arm 120 and surgical instrument 125. Computing system 140 can include at least memory, a processing unit, and user input devices, as will be described herein. Computing system 140 and tracking system 165 can also include human interface devices 145 for providing images for a surgeon to be used during surgery. Computing system 140 is illustrated as a separate standalone system, but in some examples computing system 140 can be integrated into robotic system 115. Human interface devices 145 can provide images, including but not limited to three-dimensional images of bones, glenoid, joints, and the like. Human interface devices 145 can include associated input mechanisms, such as a touch screen, foot pedals, or other input devices compatible with a surgical environment.

Computing system 140 can receive pre-operative, intra-operative and post-operative medical images. These images can be received in any manner and the images can include, but are not limited to, computed tomography (CT) scans, magnetic resonance imaging (MRI), two-dimensional x-rays, three-dimensional x-rays, ultrasound, and the like. These images in one example can be sent via a server as files attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105. Alternatively, computer system 140 can receive virtual models of the anatomy of the patient prepared remotely. Specifically, a virtual model of the anatomy of patient 110 can be created by defining anatomical points within the image(s) and/or by fitting a statistical anatomical model to the image data. The virtual model, along with virtual representations of implants, can be used for calculations related to the desired location, height, depth, inclination angle, or version angle of an implant, stem, acetabular cup, glenoid cup, total ankle prosthetic, surgical instrument, or the like to be utilized in surgical area 105. In another procedure type, the virtual model can be utilized to determine resection locations on tibia and talus bones for a total ankle arthroplasty. In a specific example, the virtual model can be used to determine a reaming angle relative to an acetabulum of a pelvis and a depth for reaming into the pelvis to place an acetabular implant. The virtual model can also be used to determine bone dimensions, implant dimensions, bone fragment dimensions, bone fragment arrangements, and the like. Any model generated, including three-dimensional models, can be displayed on human interface devices 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

Computing system 140 can also communicate with tracking system 165 that can be operated by computing system 140 as a stand-alone unit. Surgical system 100 can utilize the Polaris optical tracking system from Northern Digital, Inc. of Waterloo, Ontario, Canada. Additionally, tracking system 165 can comprise the tracking system shown and described in Pub. No. US 2017/0312035, titled "Surgical System Having Assisted Navigation" to Brian M. May, which is hereby incorporated by this reference in its entirety. Tracking system 165 can monitor a plurality of tracking elements, such as tracking elements 170, affixed to objects of interest to track locations of multiple objects within the surgical field. Tracking system 165 can function to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices. In one example, tracking elements 170 can be placed on or adjacent one or more bones of patient 110. In other examples, tracking elements 170 can be placed on robot robotic arm 120, surgical instrument 125, and/or an implant to accurately track positions within the virtual coordinate system associated with surgical system 100. In each instance tracking elements 170 can provide position data, such as patient position, bone position, joint position, robotic arm position, implant position, or the like.

Robotic system 115 can include various additional sensors and guide devices. For example, robotic system 115 can include one or more force sensors, such as force sensor 180. Force sensor 180 can provide additional force data or information to computing system 140 of robotic system 115. Force sensor 180 can be used by a surgeon to cooperatively move robotic arm 120. For example, force sensor 180 can be used to monitor impact or implantation forces during certain operations, such as insertion of an implant stem into a humeral canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures.

In order to ensure that computing system 140 is moving robotic arm 120 in a known and fixed relationship to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure. For example, a plurality of fiducial markers can be attached to patient 110, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. In additional examples, patient 110 and medical images of the patient can be registered in real space using contactless methods, such as by using a laser rangefinder held by robotic arm 120 and a surface matching algorithm that can match the surface of the patient from scanning of the laser rangefinder and the surface of the patient in the medical images. As such, the real-world, three-dimensional geometry of the anatomy attached to the fiducial markers can be correlated to the anatomy in the images and movements of instruments 125 attached to robotic arm 120 based on the images will correspondingly occur in surgical area 105.

Subsequently, other instruments and devices attached to surgical system 100 can be positioned by robotic arm 120 into a known and desired orientation relative to the anatomy. For example, robotic arm 120 can be coupled to universal instrument adapter 200 of FIG. 2, that allows multiple instruments to be attached to robotic arm without having to individually couple each instrument to robotic arm in succession and without the need for individually registering each attached instrument with the coordinate system. Robotic arm 120 can move universal instrument adapter 200 relative to anatomy of the patient such that the surgeon can, after adding and removing other instruments to the adapter as needed, perform the desired interaction with the patient at specific locations called for by the surgical plan with the attached instruments.

FIG. 2 is a schematic view of robotic arm 120 of FIG. 1 including universal instrument adapter 200, which can be positioned by robotic arm 120 relative to surgical area 105 (FIG. 1) in a desired orientation according to a surgical plan, such as a plan based on preoperative imaging. Universal instrument adapter 200 can comprise tool base 202, extension arm 204 and adapter block 206. Extension arm 204 can comprise first segment 208 and second segment 210. Adapter block 206 can comprise body 212, guide surface 214 and interface 216. In an example, adapter block 206 can be configured as a talus resection block for use in a total knee arthroplasty and, as such, adapter block 206 is also referred to herein as talus resection block 206. However, in other embodiments of universal instrument adapter 200 and surgical instrument system 300 (e.g., FIGS. 3A-3D), such instruments and components can be configured to facilitate performing of other surgical procedures, such as knee, shoulder and hip arthroplasties. As such, universal instrument adapter 200 can be universal to a particular procedure. However, in additional examples, universal instrument adapter 200 can be universal to multiple procedures, with sets of attachment instruments attached thereto being specific to particular procedures.

Robotic arm 120 can include joint 135A that permits rotation about axis 216A, joint 135B that can permit rotation about axis 216B, joint 135C that can permit rotation about axis 216C and joint 135D that can permit rotation about axis 216D.

In order to position universal instrument adapter 200 relative to anatomy of patient 110 (FIG. 1), surgical system 100 (FIG. 1) can manipulate robotic arm 120 automatically by computing system 140 or a surgeon manually operating computing system 140 to move universal instrument adapter 200 to the desired location, e.g., a location called for by a surgical plan to align an instrument relative to the anatomy. For example, robotic arm 120 can be manipulated along axes 216A-216D to position universal instrument adapter 200 such that adapter block 206 is located in a desired location relative to the anatomy. As such, a step of a surgical procedure can be performed, such as by using guide surface 214. However, subsequent steps of the surgical procedure can be performed with universal instrument adapter 200 without having to uncouple adapter 200 from robotic arm 120. For example, other instruments can be attached to block 206 at interface 216. Other instruments attached at interface 216 can be used without having to re-register an additional instrument to the coordinate system because the dimensions and geometries of universal instrument adapter 200 and other instruments to be used therewith can be known by surgical system 100 (FIG. 1) such that the locations of block 206 and instruments attached thereto can be calculated by system 100 as robotic arm 120 moves throughout the coordinate system.

Figure 9:
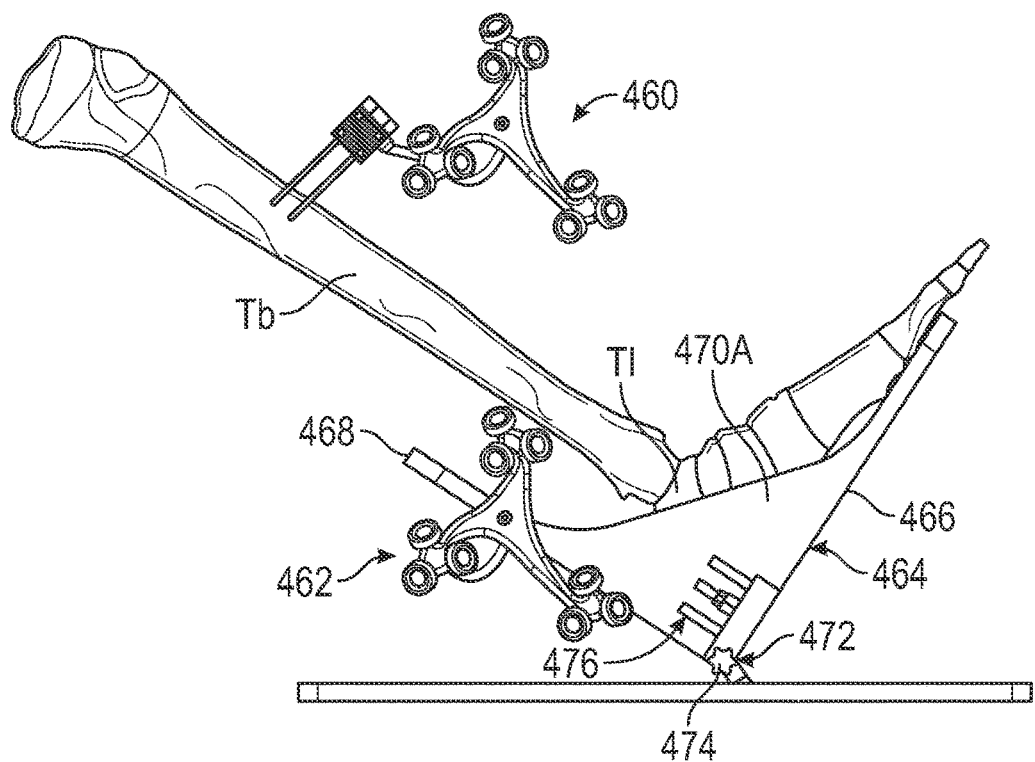
FIG. 9 is a schematic diagram of a pair of tracking elements and a lower leg comprising a tibia and a talus positioned in an alignment boot.

Robotic arm 120 can be separately registered to the coordinate system of surgical system 100, such via use of a tracking element 170 (FIG. 1). Fiducial markers can additionally be separately registered to the coordinate system of surgical system 100 via engagement with a probe having a tracking element 170 attached thereto. Universal instrument adapter 200 can be registered to the coordinate system via coupling with robotic arm. Other components, such as tibia Tb and alignment boot 464 (FIG. 9), can be registered using trackers 460 and 462 (FIG. 9). As such, some or all of the components of surgical system 100 can be individually registered to the coordinate system (with or without the aid of tracking elements) and, if desired, movement of such components can be continuously or intermittently tracked with a tracking element 170.

In some robotic procedures, instruments can be separately and individually tracked using an optical navigation system that, under ideal conditions, alleviate the need for precisely maintaining the location of an instrument, such as body 212, through a surgical procedure or surgical task, as the optical navigation system can provide the surgical computer system information to compensate for any changes. However, as optical navigation systems require line-of-sight with the instruments to be maintained, there is a significant advantage in not requiring instruments to be navigated (or at least not constantly navigated). Universal instrument adapter 200 allows multiple instruments to be registered to robotic system 115 without the need for individually tracking each instrument. Robotic system 115 can know the precise location of robotic arm 120, and the geometry and dimensions of universal instrument adapter 200 can be registered to robotic system 115. As such, the location of adapter block 206 in the surgical space can be determined as robotic arm 120 moves adapter block 206 within the surgical space. Furthermore, robotic system 115 can be provided with the geometry and dimensions of instruments configured to be attached to adapter block 206 such that the locations of attachment instruments can also be tracked as robotic arm 120 move. Thus, individual tracking or registration of the attachment instruments can be avoided.

FIGS. 3A-3D are perspective views of surgical instrument system 300 including universal instrument adapter 200, tibia resection block 302, talar trial system 304 and talus reaming guide 306. Talar trail system 304 can comprise talar adapter 308 and talar trial 310. Adapter block 206 of universal instrument adapter 200 can be configured as a talus resection block. As such, talus resection block 206, tibia resection block 302, talar trial system 304 and talus reaming guide 306 can together form a set of instruments configured to perform a total ankle arthroplasty. Each of tibia resection block 302, talar trial system 304 and talus reaming guide 306 can be configured as attachable or accessory instruments that can be coupled to adapter block 206. As such, only universal instrument adapter 200 needs to be attached to robotic arm 120, and only universal instrument adapter 200 needs to be registered to the coordinate system of surgical system 100. As such, fewer instruments are required to perform the total ankle arthroplasty, as compared to conventional systems, and robotic arm 120 can be relied upon to provide precise aligning of universal instrument adapter 200 and any accessory instruments attached thereto.

Figure 3A:
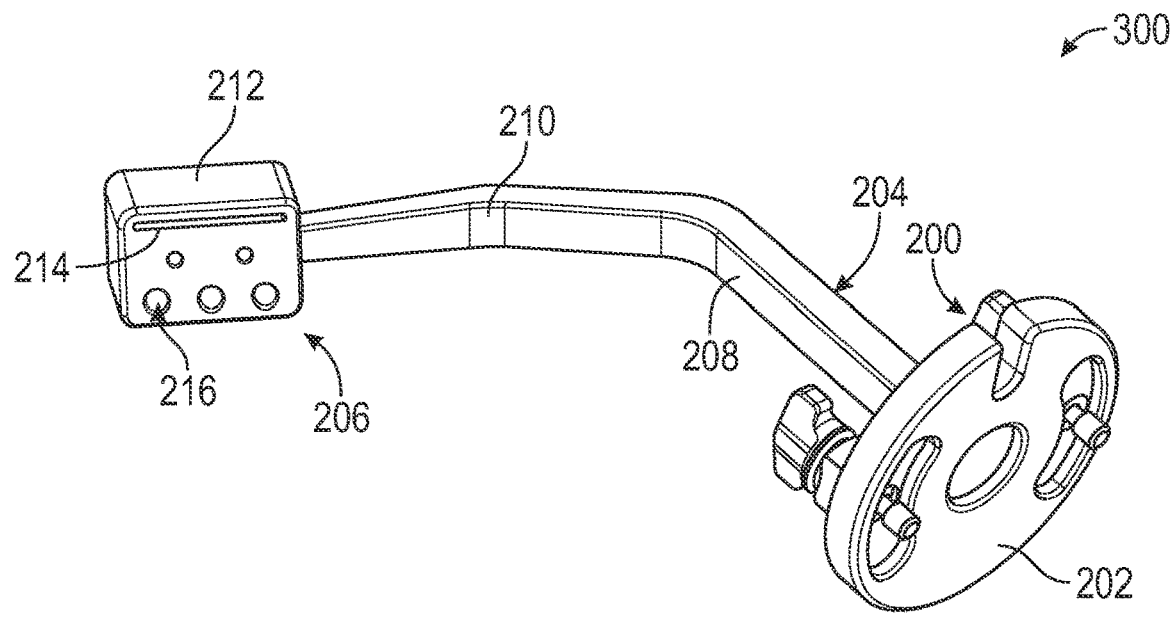
FIG. 3A is a perspective view of a talus resection instrument comprising an attachment plate, an extension arm and a talus resection block, which can comprise a universal instrument adapter.

FIG. 3A is a perspective view of universal instrument adapter 200 comprising a talus resection instrument comprising tool base 202, extension arm 204 and adapter block 206, which can comprise a talus resection block. As discussed in greater detail below with reference to FIGS. 4A-4C, adapter block 206 can comprise both an instrument and an adapter for attaching other instruments to extension arm 204 and, hence, robotic arm 120. For example, guide surface 214 can comprise a slot for guiding or otherwise engaging a cutting instrument such as a reciprocating or oscillating saw blade to cut bone, such as a superior portion of a talus. Interface 216 can comprise features that facilitate attachment of other instruments to adapter block 206, such as ports, plugs, receptacles, threaded couplers, slots and the like. In examples, interface 216 can comprise one or more through-bores, threaded bores, dovetail slots, pins, detents, chuck mechanisms and collets, and combinations thereof.

Figure 3B:
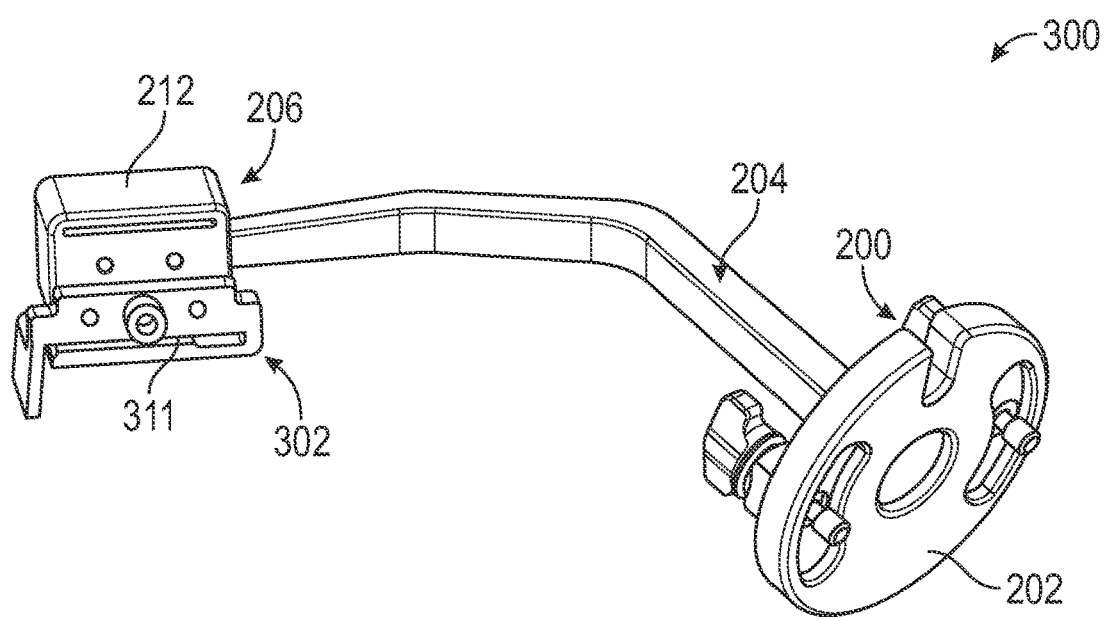
FIG. 3B is a perspective view of the talus resection instrument with a tibia resection block attached to the talus resection block.

FIG. 3B is a perspective view of universal instrument adapter 200 with tibia resection block 302 attached to talus resection block 206. As discussed in greater detail below with reference to FIGS. 5A-5D, tibia resection block 302 can comprise a feature for guiding another surgical instrument, such as slot 311 for guiding or otherwise engaging a cutting instrument such as a reciprocating or oscillating saw blade to cut bone, such as an inferior portion of a tibia.

Figure 3C:
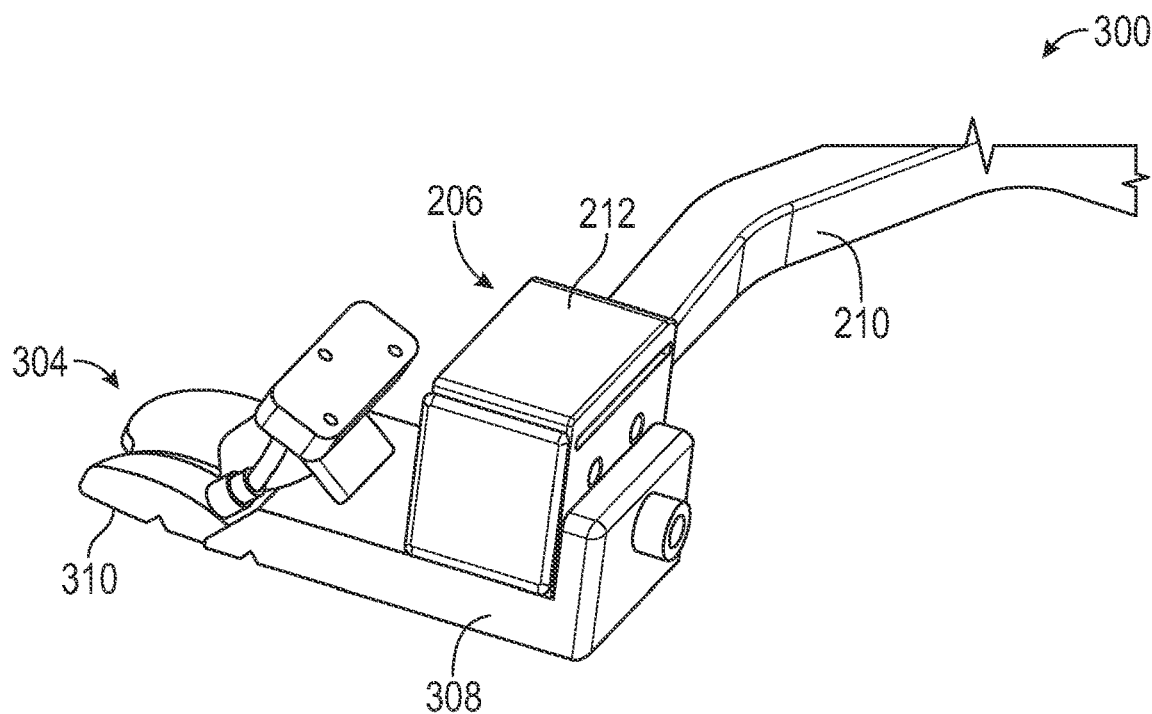
FIG. 3C is a perspective view of the talus resection instrument with a trial implant attached to the talus resection block.

FIG. 3C is a perspective view of universal instrument adapter 200 with talar trial system 304 attached to talus resection block 206. Talar adapter 308 can be directly coupled to talus resection block 206 and talar trial 310 can be attached to talar adapter 308. As discussed in greater detail below with reference to FIGS. 6A-6D, talar trial system 304 can comprise a system for inserting a trial talus prosthetic in between a reamed distal end of a tibia and a reamed proximal end of a talus to, for example, verify accuracy of the resections. For example, the geometry of talar trial 310 can match that of a prosthetic talar device, such as talar bearing component 66 (FIG. 8D), to verify or confirm proper fit. Also, talar adapter 308 can include indicator notch 408 (FIG. 6A) and talar trial 310 can include indicator notch 392 (FIG. 6A) to verify or confirm anterior-posterior placement of the prosthetic talar device.

Figure 3D:
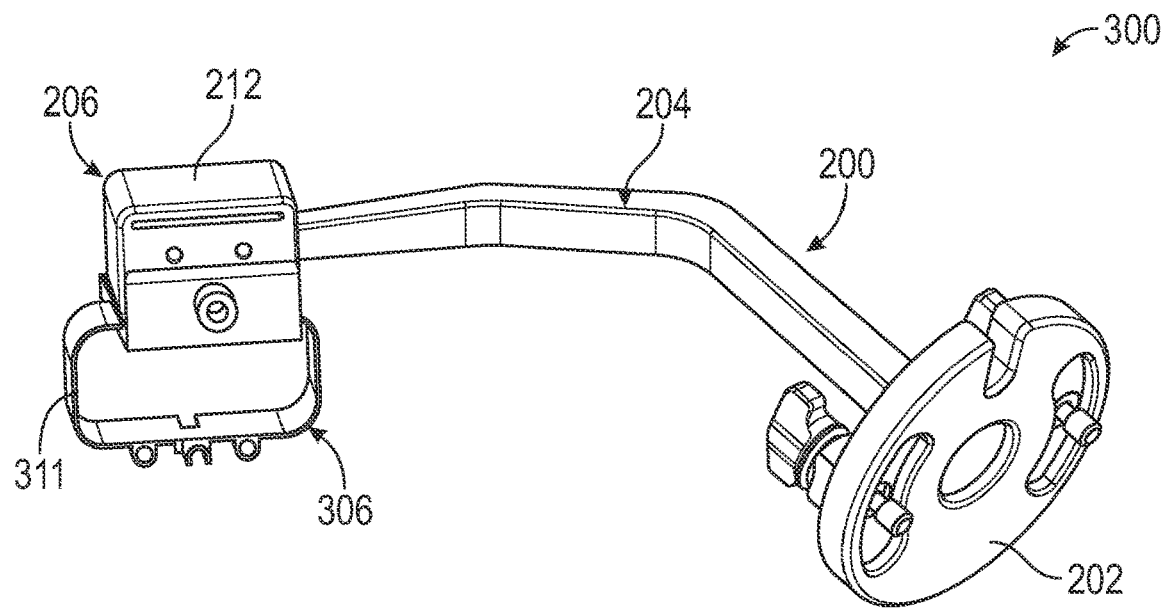
FIG. 3D is a perspective view of the talus resection instrument with a talus reaming guide attached to the talus resection block.

FIG. 3D is a perspective view of universal instrument adapter 200 with talus reaming guide 306 attached to talus resection block 206. As discussed in greater detail below with reference to FIGS. 7A-7C, talus reaming guide 306 can comprise a feature for guiding another surgical instrument, such as hoop 314 for guiding or otherwise engaging a cutting instrument such as a reciprocating or oscillating reamer to cut bone, such as an anterior portion of a talus.

As discussed below with reference to FIGS. 9-15, talus resection block 206, tibia resection block 302, talar trial system 304 and talus reaming guide 306 can be used in one or more sequences to perform a total ankle arthroplasty to implant prosthetic ankle device 60 of FIGS. 8A-8D.

Figure 4A:
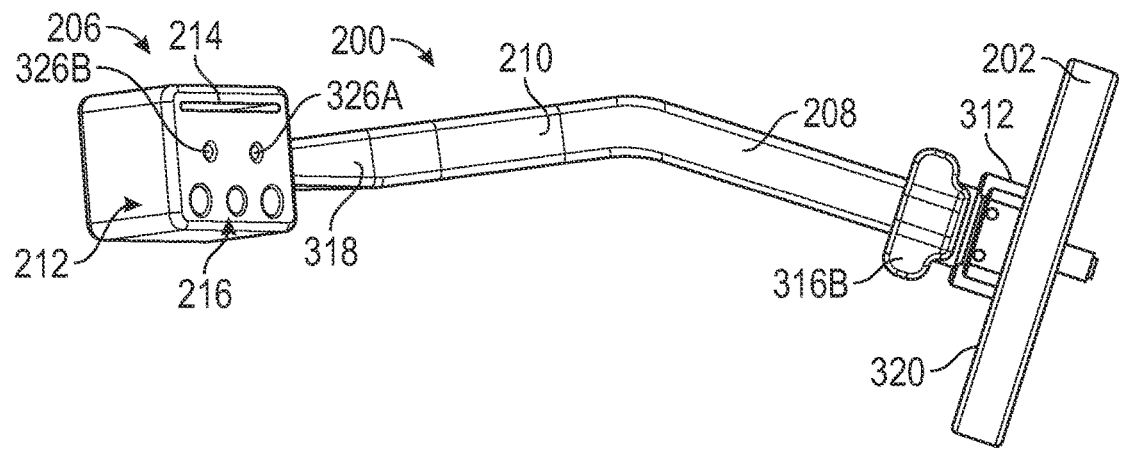
FIG. 4A is a perspective view of the talus resection instrument of FIG. 3A.
Figure 4B:
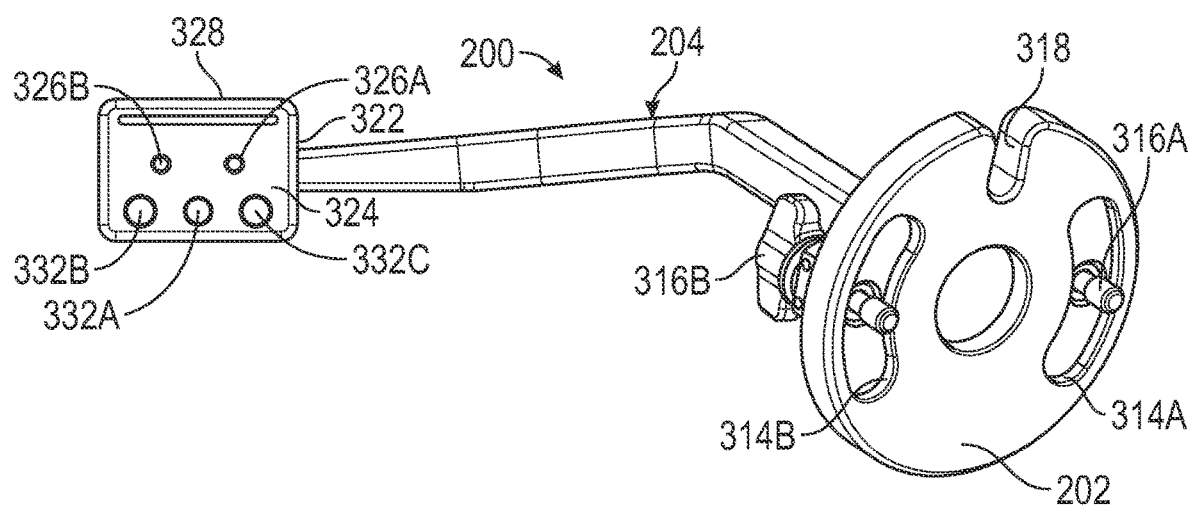
FIG. 4B is a plan view of the talus resection instrument of FIG. 4A showing a front view of the talus resection block.
Figure 4C:
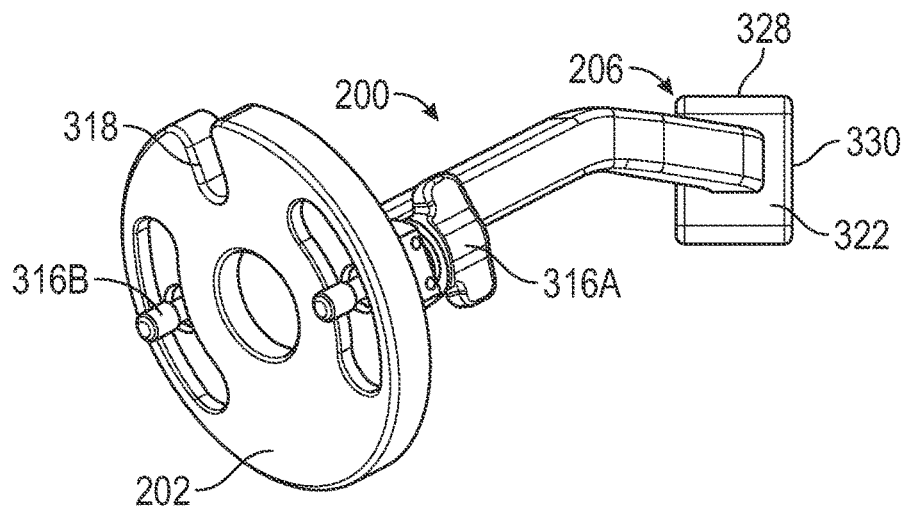
FIG. 4C is a plan view of the talus resection instrument of FIG. 4A showing a side view of the talus resection block.

FIG. 4A is a perspective view of universal instrument adapter 200 of FIG. 2 configured as a talus resection instrument. FIG. 4B is a plan view of universal instrument adapter 200 of FIG. 4A showing a front view of talus resection block 206. FIG. 4C is a plan view of universal instrument adapter 200 of FIG. 4A showing a side view of talus resection block 206. FIGS. 4A-4C are discussed concurrently.

Tool base 202 (FIG. 2) can comprise pedestal 312 from which extension arm 204 can extend, mounting slots 314A and 314B and fasteners 316A and 316B. Tool base 202 can be coupled to robotic arm 120 by inserting fasteners 316A and 316B through mounting bores 314A and 314B and into mating bores in robotic arm 120. Slot 318 can receive an alignment feature on robotic arm 120 to ensure proper mounting of tool base 202.

Extension arm 204 can comprise first segment 208 and second segment 210, which can include third segment 318. Segments 208, 210 and 318 can comprise elongate rigid members extending from tool base 202 in an end-to-end fashion. Segments 208, 210 and 318 can be configured to hold resection block 206 in a fixed position relative to tool base 202. Segments 208, 210 and 318 can be tubular or solid bodies that are angled relative to each other to position resection block 206 relative to tool base 202, such as in a position conducive for a surgeon to access resection block 206 while robotic arm 120 is out of the way of the surgeon. In an example, first segment 208 can extend from tool base 202 perpendicular, or approximately perpendicular, to front surface 320 of tool base 202, third segment 318 can extend from resection block 206 perpendicular, or approximately perpendicular, to side surface 322 of resection block 206, and second segment 210 can couple first and third segments 208 and 318. Second segment 210 can thus be disposed at angles relative to first and third segments 208 and 318. In other examples, segments 208, 210 and 318 can comprise curved segments. In an example, second segment 210 can couple first and third segments 208 and 318 such that front surface 324 of resection block 206 is at an angle of approximately thirty degrees to front surface 320. In various examples, segments 208, 210 and 318 can lie in a common plane or can be in planes oblique to each other. Additionally, third segment 318 can taper down toward resection block 206 to reduce the footprint against resection block 206.

Resection block 206 can comprise body 212 that provides a platform for guide surface 214 and interface 216. Body 212 can further comprise bores 326A and 326B.

Guide surface 214 can comprise a planar surface against which a cutting instrument can be engaged to perform a cutting procedure. In the illustrated example, guide surface 214 can comprise a slot that is bounded on four sides, e.g., front surface 324 can provide upper, lower and lateral sides around guide surface 214. However, in other examples, guide surface 214 can comprise an unbounded ledge or a partially bounded ledge, e.g., a partial slot. Guide surface 214 can be located toward a side of body 212 to increase visibility of anatomy behind resection block 206. For example, guide surface 214 can be located proximate to top surface 328 such that a surgeon can view anatomy over the top of resection block 206 while simultaneously allowing the lower portion of body 212 to include bores 326A and 326B and interface 216.

Bores 326A and 326B can comprise through bores extending from front surface 324 all the way through to rear surface 330. Bores 326A and 326B can thus provide ports for inserting pins through body 212 and into the anatomy of the patient. The pins can be used to, for example, anchor resection block 206 while cutting of bone occurs to ensure a straight cut.

Interface 216 can comprise means for facilitating coupling of another instrument to resection block 206. Interface 216 can comprise a socket having one or more receptacles for receiving mating components on an additional instrument. In the illustrated example, interface 216 can comprise bores 332A, 332B and 332C. Bores 332A-332C can comprise through-bores extending from front surface 324 to rear surface 330. Bores 332A-332C can comprise multiple points of contact between resection block 206 and a mating instrument to facilitate rotational alignment. In examples, one or more of bores 332A-332C can be threaded to receive a complimentary threaded shaft or fastener. For example, bore 332A can be threaded to receive a threaded fastener extending from an additional instrument and bores 332B and 332C can be simple through-bores to receive alignment prongs of the additional instrument.

Figure 5A:
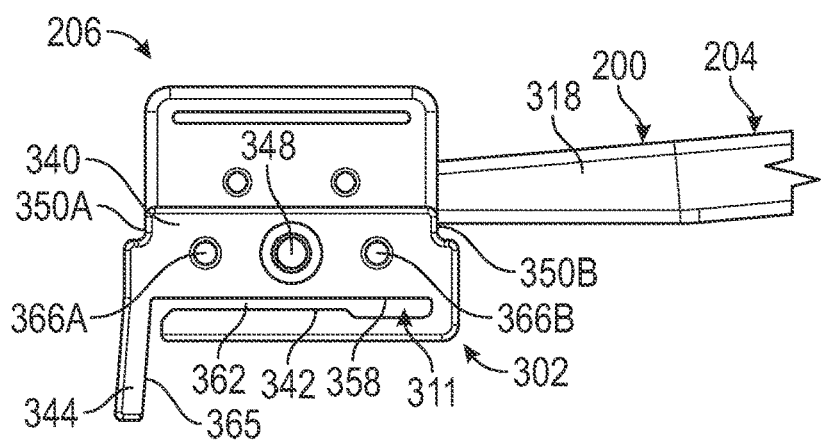
FIG. 5A is a front view of the talus resection instrument of FIG. 3B with the tibia resection block attached thereto.
Figure 5B:
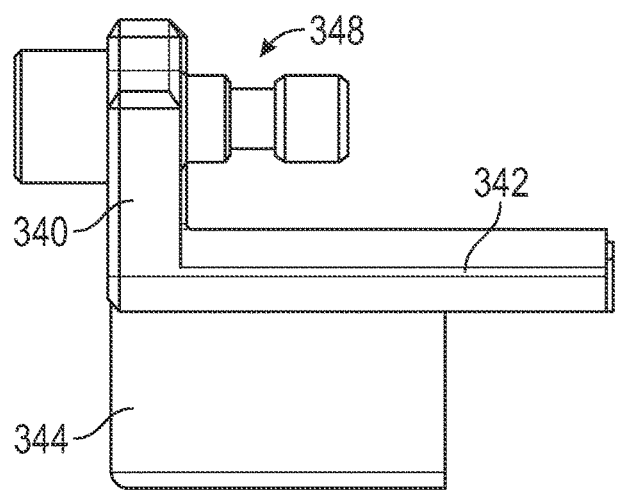
FIG. 5B is a side view of the tibia resection block of FIG. 5A.
Figure 5C:
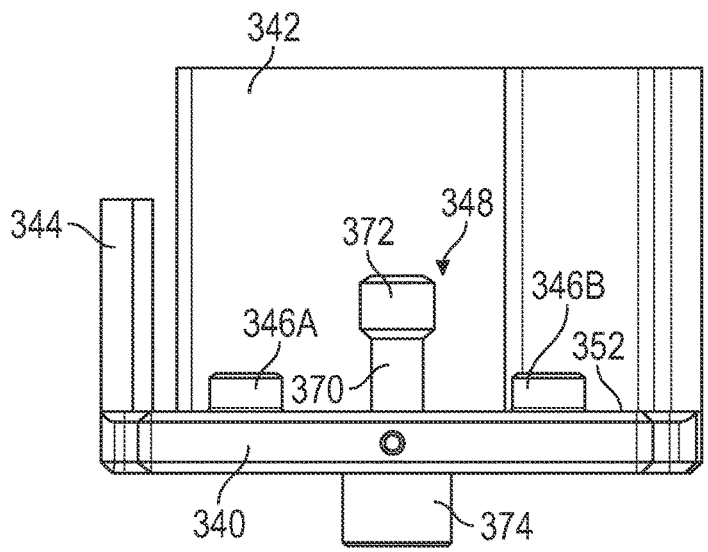
FIG. 5C is a top view of the tibia resection block of FIG. 5A.
Figure 5D:
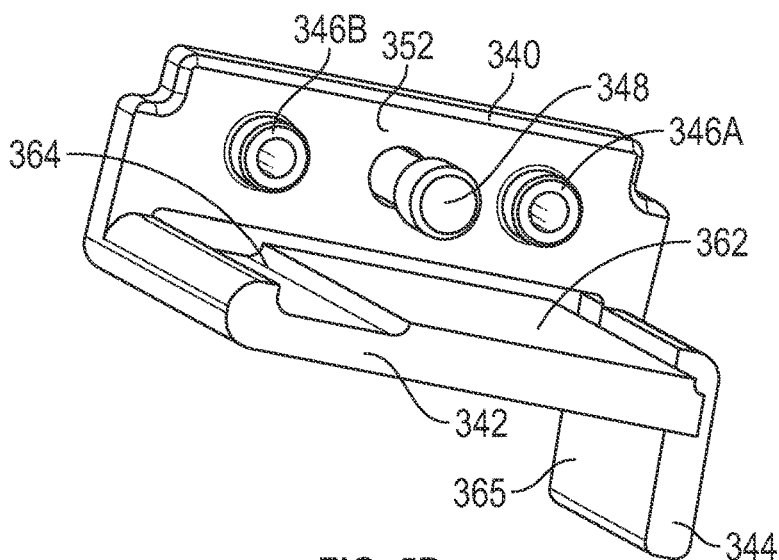
FIG. 5D is a perspective view of the tibia resection block of FIG. 5A.

FIG. 5A is a front view of universal instrument adapter 200 of FIG. 3B configured as a talus resection instrument with tibia resection block 302 attached thereto. FIG. 5B is a side view of tibia resection block 302 of FIG. 5A. FIG. 5C is a top view of tibia resection block 302 of FIG. 5A. FIG.

5D is a perspective view of tibia resection block 302 of FIG. 5A. FIGS. 5A-5D are discussed concurrently.

Tibia resection block 302 can be coupled to talus resection block 206 of universal instrument adapter 200. Talus resection block 206 can extend from third segment 318 of extension arm 204. Tibia resection block 302 can comprise anterior panel 340, inferior panel 342, side panel 344, first pin boss 346A, second pin boss 346B and fastener 348.

Anterior panel 340 can comprise a plate having notches 350A and 350B for providing alignment features, such as to verify alignment of tibia resection block 302 with talus resection block 206. Anterior panel 340 can be a planar body having posterior surface 352 for engaging front surface 324 (FIG. 4B) of resection block 206. Inferior surface 358 of anterior panel 340 can comprise a cutting guide surface that forms partially-bounded cutting guide slot 311 along with superior surface 362 of inferior panel 342.

Inferior panel 342 can be a planar body or plate having superior surface 362 that can extend back underneath talus resection block 206. As such, superior surface 362 can comprise an elongate cutting guide surface against which a cutting instrument, such as a saw blade can rest, slide, oscillate or reciprocate. Inferior panel 342 can additionally include trough 364 to facilitate insertion of pins and cutting instruments within cutting guide slot 311.

Side panel 344 can comprise a planar body or flange extending down from anterior panel 340 past inferior panel 342. Side panel 344 can comprise side surface 365 that can comprise a cutting guide surface. In examples, inferior surface 358 and superior surface 362 can be parallel to each other and side surface 365 can be angled relative to surfaces 358 and 362.

Pin bosses 346A and 346B can extend from posterior surface 352 of anterior panel 340. Pin bosses 346A and 346B can comprise cylindrical bodies forming through-bores. Pin bosses 346A and 346B can align with bores 366A and 366B extending through anterior panel 340. The axes of pin boss 346A and bore 366A and pin boss 346B and bore 366B can align respectively and the axes of bores 366A and 366B can be parallel. Furthermore, the axes of bores 366A and 366B can be parallel to surface 362. Pin bosses 346A and 346B can engage bores 332B and 332C (FIG. 4B) to position resection block 302 against resection block 206. Bores 366A and 366B can thus provide ports for inserting pins through anterior panel 340 and into the anatomy of the patient. The pins can be used to, for example, anchor resection block 302 while cutting of bone occurs to ensure a straight cut.

Fastener 348 can comprise a projection for engaging resection block 206, such as at bore 332A (FIG. 4B). Fastener 348 can comprise shaft 370, head 372 and knob 374. In examples, shaft 370 can extend through a bore within anterior panel 340 and knob 374 can be separately attached to shaft 370. Thus, fastener 348 can be rotatable within anterior panel 340, but can be immobilized with the use of a fastener or set-screw, as shown in FIG. 5C. Head 374 can comprise a threaded body integral with shaft 370 for coupling to bore 332A, which, in examples, can be complimentarily threaded for engagement with thread on head 372. Knob 374 can include a hex socket (FIG. 5A), or some other torque transferring engagement, to receive a tool for rotating fastener 348 to facilitate coupling of head 374 with bore 332A.

Pin bosses 346A and 346B can be fit into bores 332B and 332C of talus resection block 206, as shown in FIG. 4B. Likewise, shaft 370 of fastener 348 can be inserted into bore 332A. In examples, head 372 can be threaded into bore 332A. As such, tibia resection block 302 can be rigidly attached to talus resection block 206 to allow accurate cutting through slot 311.

Figure 6A:
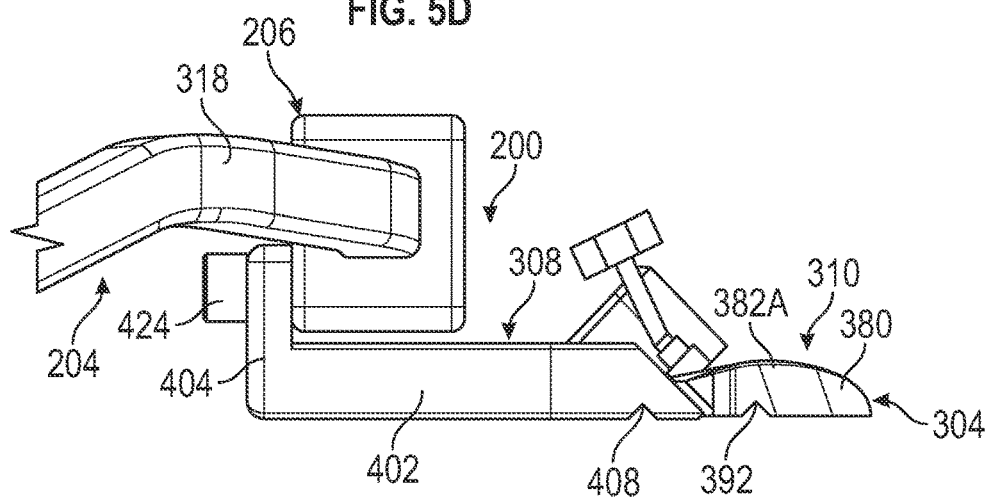
FIG. 6A is a side view of the talus resection instrument of FIG. 3C with the trial implant attached thereto via a trial holder.
Figure 6B:
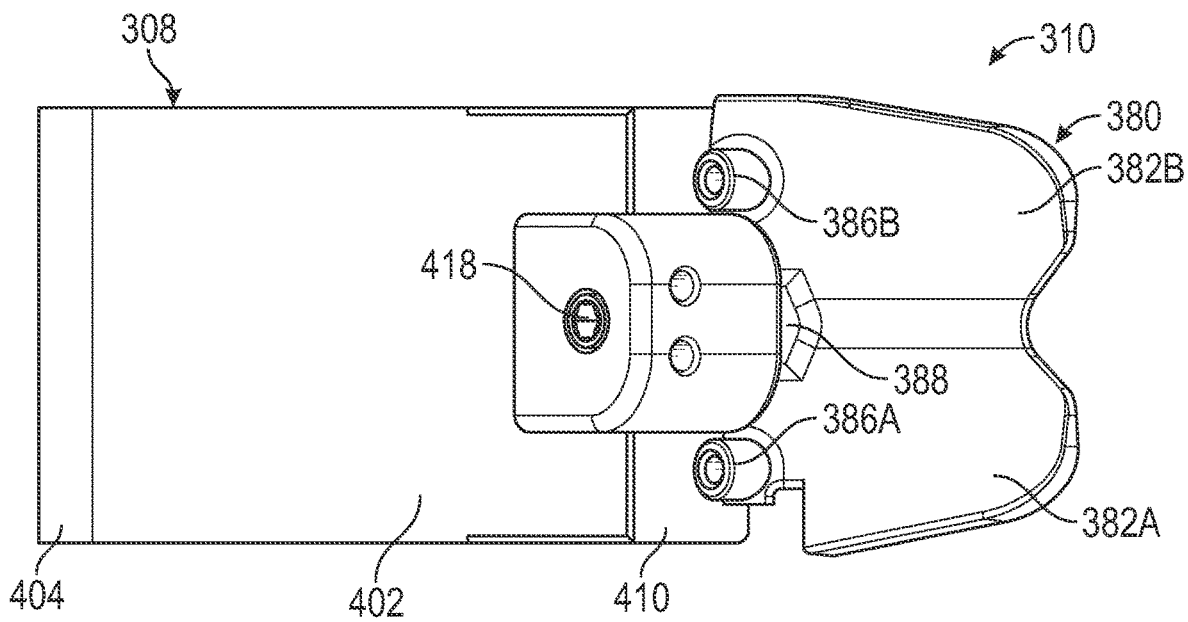
FIG. 6B is a top view of the trial implant and trial holder of FIG. 6A.
Figure 6C:
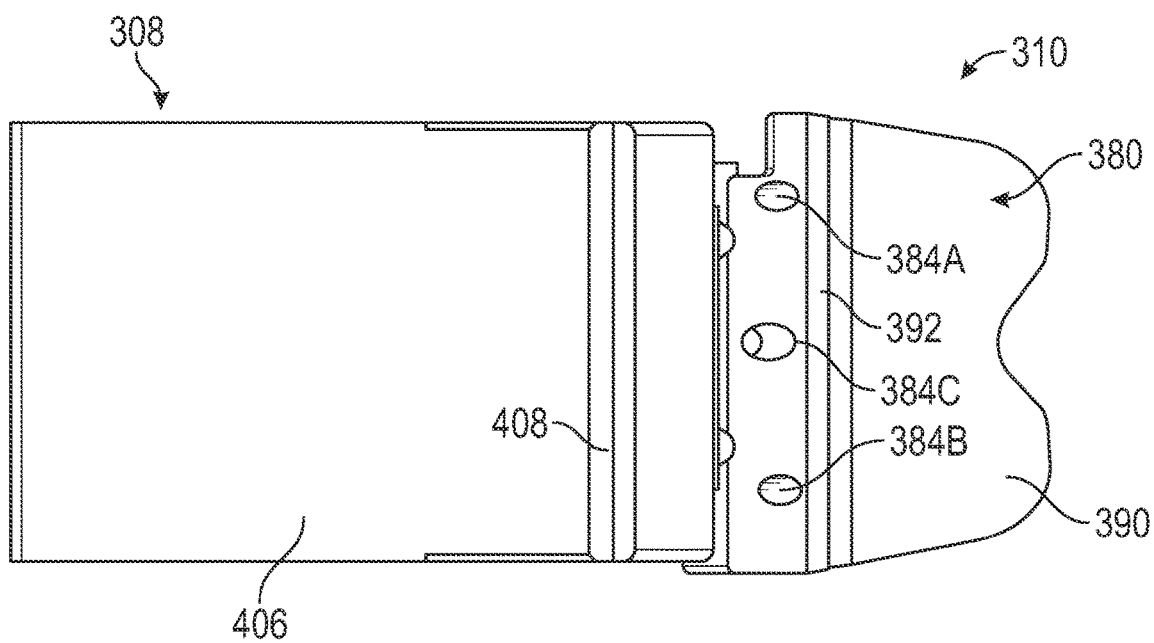
FIG. 6C is a bottom view of the trial implant and trial holder of FIG. 6A.
Figure 6D:
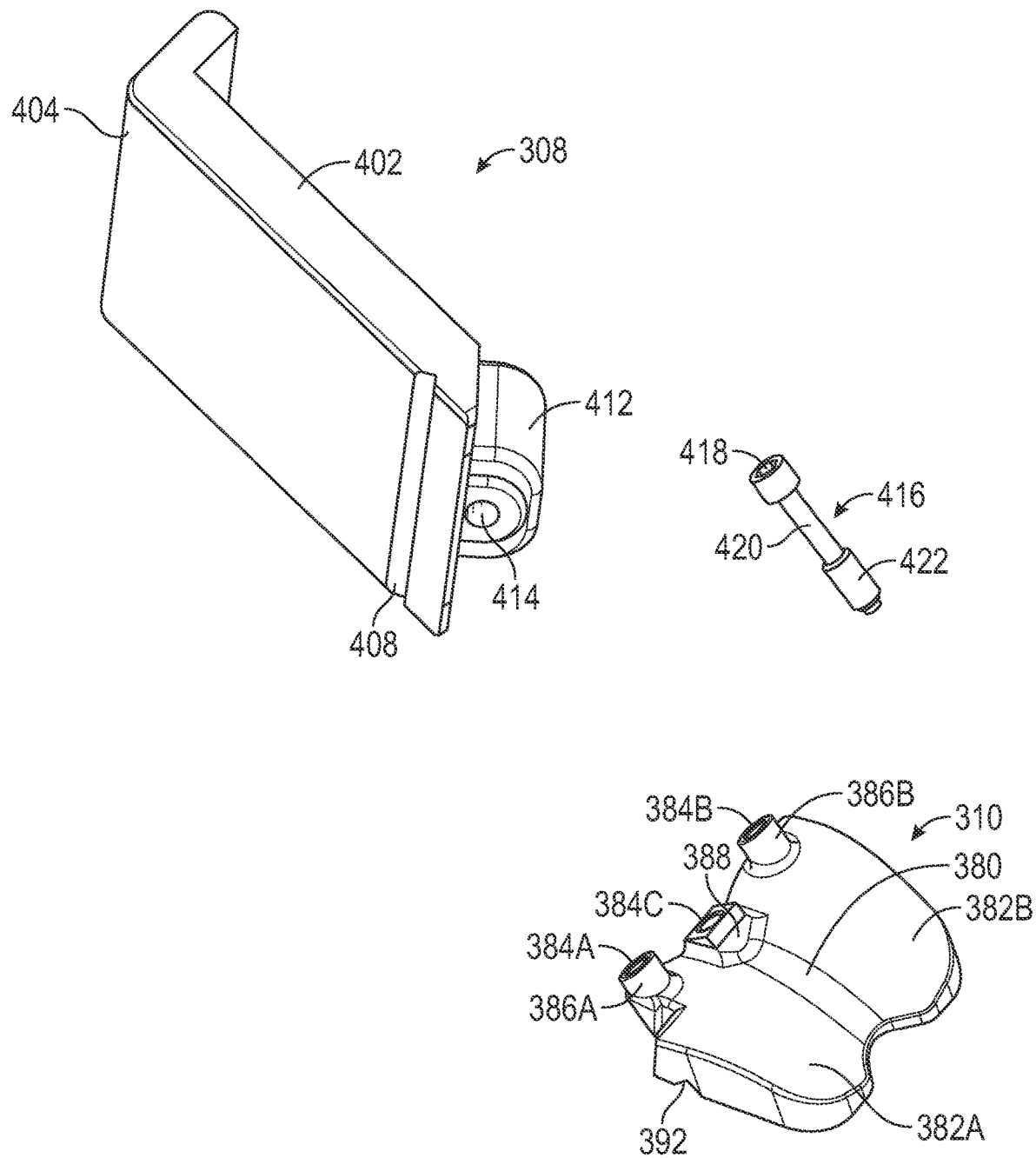
FIG. 6D is a perspective view of the trial implant and trial holder of FIG. 6A.

FIG. 6A is a side view of universal instrument adapter 200 of FIG. 3C configured as a talus resection instrument of FIG. 3C with trial implant 310 attached thereto via trial holder 308. FIG. 6B is a top view of trial implant 310 and trial holder 308 of FIG. 6A. FIG. 6C is a bottom view of trial implant 310 and trial holder 308 of FIG. 6A. FIG. 6D is a perspective view of the trial implant 310 of FIG. 6A. FIGS. 6A-10D are discussed concurrently.

Talar trial implant 310 can comprise trial body 380, first condyle 382A, second condyle 382B, bores 384A, 384B and 384C, collars 386A and 386B, socket 388, inferior surface 390 and first indicator notch 392. Trial holder 308 can comprise interface body 402, flange 404, inferior surface 406, second indicator notch 408, engagement face 410, fastener block 412 and fastener bore 414. Talar trial implant 310 and trial holder 308 can be coupled together using fastener 416, which can comprise head 418, shaft 418 and threaded portion 420.

Talar trial implant 310 can be coupled to trial holder 308, which can be coupled to talus resection block 206 via fastener 424. Flange 404 can include a bore for receiving fastener 424 and can also include pin bosses similar to pin bosses 346A and 346B (FIG. 5C). Robotic arm 120 can be used to insert talar trial implant 310 between a resected tibia and talus such that inferior surface 390 is positioned adjacent a resected surface of talus Tl (FIG. 9). Indicator notches 392 and 408 can be viewed by a surgeon to evaluate the anterior-posterior placement of talar trial implant 310 to thereby evaluate the resected surfaces. Condyles 382A and 382B can additionally be engaged with a prosthetic tibial bearing component, such as tibial tray component 64 of FIG. 8A2, to evaluate eventual placement of talar bearing component 66 (FIG. 8D). If a surgeon determines via the evaluation process that talar trial implant 310 is improperly or unsatisfactorily positioned, additional resetting of talus Tl and tibia Tb (FIG. 9) can be performed, or the surgical plan can be modified as deemed appropriate.

Figure 7A:
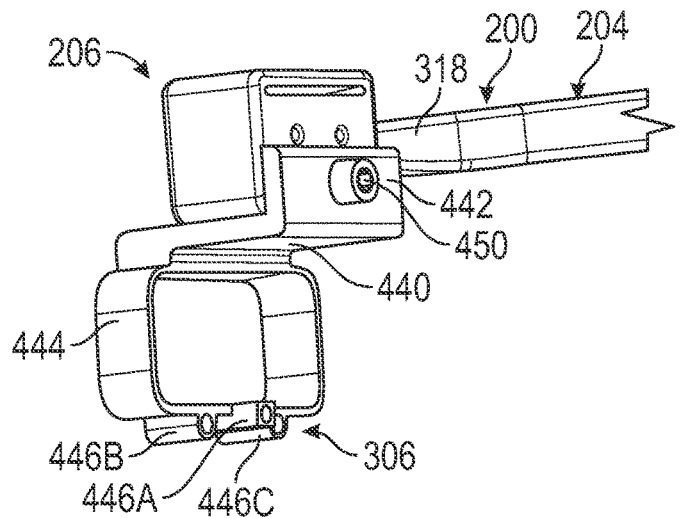
FIG. 7A is a perspective view of the talus resection instrument of FIG. 3C with the talus reaming guide attached thereto.
Figure 7B:
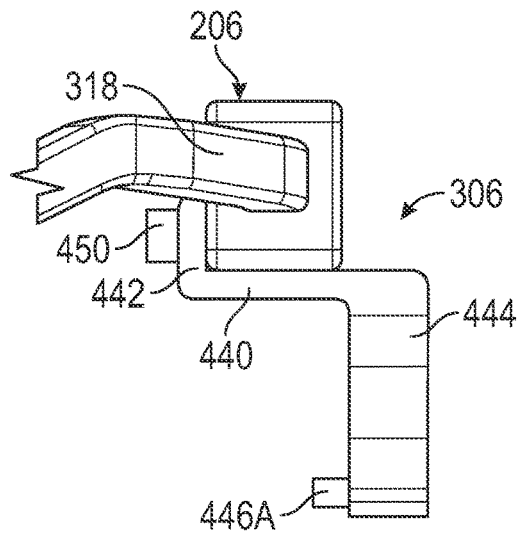
FIG. 7B is a side view of the talus reaming guide of FIG. 7A.
Figure 7C:
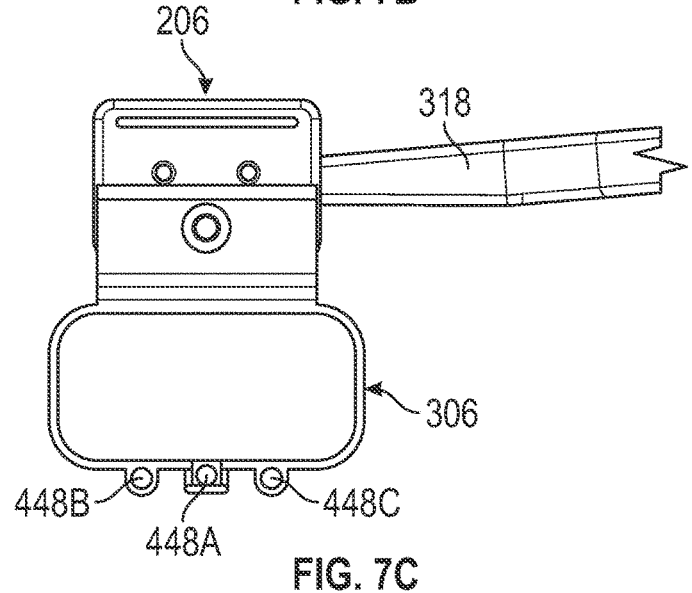
FIG. 7C is a front view of the talus reaming guide of FIG. 7A.

FIG. 7A is a perspective view of universal instrument adapter 200 of FIG. 3C configured as a talus resection instrument of FIG. 3C with talus reaming guide 306 attached thereto. FIG. 7B is a side view of talus reaming guide 306 of FIG. 7A. FIG. 7C is a front view of talus reaming guide 306 of FIG. 7A. FIGS. 7A-7C are discussed concurrently.

Talus reaming guide 306 or block 302 (FIG. 5A) can be coupled to talus resection block 206 of universal instrument adapter 200. Talus resection block 206 can extend from third segment 318 of extension arm 204.

Talus reaming guide 306 can comprise mounting plate 440, mounting plate 442, guide hoop 444, flange 446A, flange 446B and flange 446C. Flanges 446A, 446B and 446C can include bores 448A, 448B and 448C, respectively. Fastener 450 can be used to couple talus reaming guide 306 to talus resection block 206. Mounting plate 442 can include a bore for receiving fastener 450 and can also include pin bosses similar to pin bosses 346A and 346B (FIG. 5C).

Mounting plate 440 and mounting plate 442 can provide means for attaching talus reaming guide 306 to talus resection block 206. Fastener 348 (FIGS. 5A-5D) can be inserted into bore 332A (FIG. 4B) to rigidly attach talus reaming guide 306 to talus resection block 206 to allow accurate reaming within guide hoop 444. Guide hoop 444 can comprise a template that bounds a portion of talus Tl to be reamed to engage talar bearing component 66 (FIG. 8D). Bores 448A, 448B and 448C can provide ports for inserting pins through guide hoop 444 and into the anatomy of the patient. The pins can be used to, for example, anchor talus reaming guide 306 while reaming of bone occurs to ensure a straight cut.

Figure 8A:
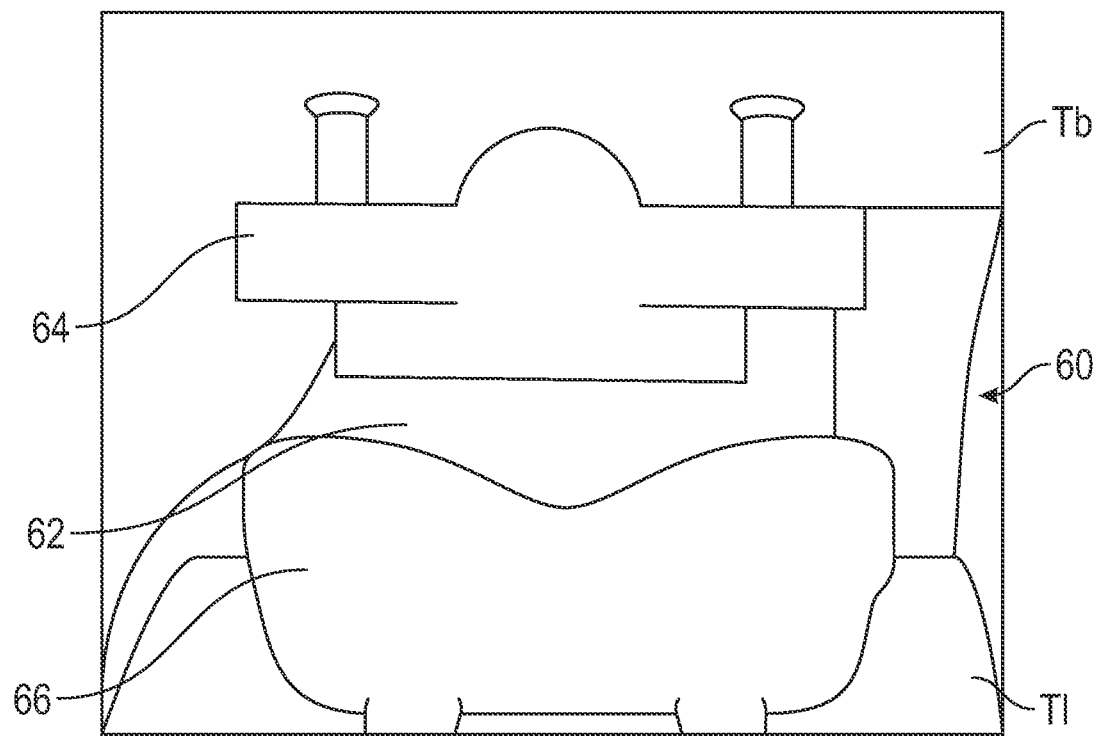
FIG. 8A is a schematic view of a prosthetic ankle component implanted in tibia and talus bones.
Figure 8B:
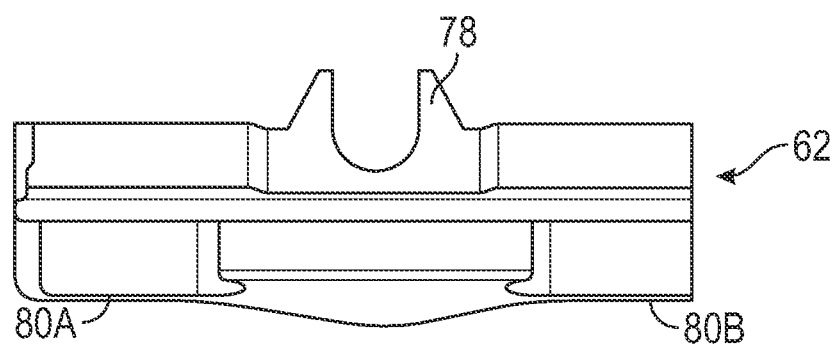
FIGS. 8B, 8C and 8D are perspective views of a tibial bearing component, a tibial tray component, and a talar bearing component, respectively, of the prosthetic ankle component of FIG. 8A, for use as a total ankle arthroplasty prosthetic that can be implanted with the instruments of FIGS. 3A-3D.
Figure 8C:
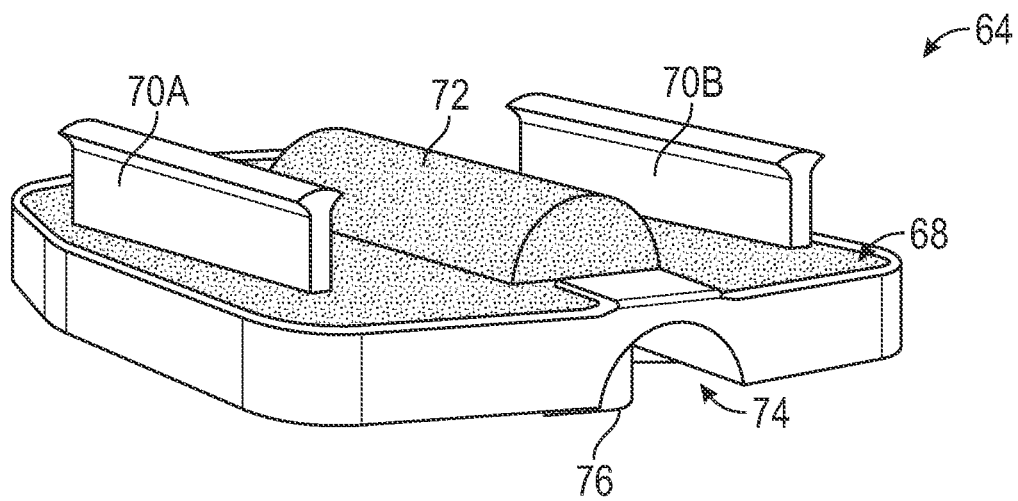
Figure 8D:
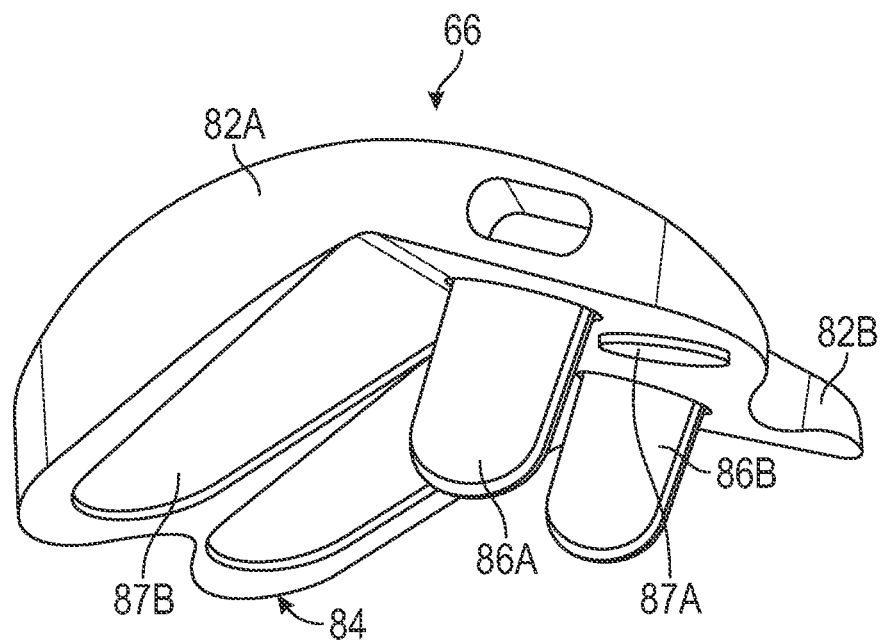

FIG. 8A is perspective view of prosthetic ankle device 60 for use as a total ankle arthroplasty prosthetic that can be implanted with surgical instrument system 300 of FIGS. 3A-3D. FIGS. 8B, 8C and 8D are perspective views of tibial bearing component 62, tibial tray component 64, and talar bearing component 66, respectively, that together form prosthetic ankle device 60.

As shown in FIG. 8A, tibial tray component 64 can be attached to tibia Tb and talar bearing component 66 can be attached to talus Tl. Tibial bearing component 62 can be attached to tibial tray component 64 for engagement with talar bearing component 66.

With reference to FIG. 8C, tibial tray component 64 can comprise bone-facing side 68 that can include fixation devices 70A and 70B and protrusion 72. Bone-facing side 68 can include a layer of porous material and protrusion 72 can be formed of porous material to facilitate bone ingrowth. Tibial tray component 64 can also comprise attachment side 74 that can include attachment feature 76 for engaging tibial bearing component 62.

With reference to FIG. 8B, tibial bearing component 62 can comprise attachment feature 78 for engaging attachment feature 76. In examples, attachment features 76 and 78 can comprise a snap-fit interface or any other suitable device for attaching tibial bearing component 62 and tibial tray component 64 into a locked configuration such that movement therebetween is inhibited. Tibial bearing component 62 can additionally include bearing surfaces 80A and 80B. Bearing surfaces 80A and 80B can be shaped to provide a smooth interface against which talar bearing component 66 can side against. Tibial bearing component 62 can be configured in different sizes to accommodate different sized ankle joints for different patients.

With reference to FIG. 8D, talar bearing component 66 can comprise bearing surfaces 82A and 82B that can engage bearing surfaces 80A and 80B, respectively. In examples, bearing surfaces 80A and 80B can be shaped as condyles, or smooth humps, to engage concavities formed by bearing surfaces 80A and 80B. Talar bearing component 66 can comprise bone-facing side 84 that can include fixation features 86A and 86B. Bone-facing side 84 can further comprise first surface 87A and second surface 87B. Talar bearing component 66 can be configured in different sizes to accommodate different sized ankle joints for different patients.

FIG. 9 is a schematic diagram of tracking elements 460 and 462 and lower leg comprising tibia Tb and talus Tl positioned in alignment boot 464.

Tracking elements 460 and 462 can be configured similarly as tracking elements 170 of FIG. 1. Tracking system 165 (FIG. 1) can monitor tracking elements 460 and 462, affixed to tibia Tb and alignment boot 464, respectively, to track locations of multiple objects within the surgical area 105 (FIG. 1). Tracking system 165 can function to create a virtual three-dimensional coordinate system within surgical area 105 for tracking patient anatomy, surgical instruments such as surgical instrument system 300, or portions of robotic system 115.

Alignment boot 464 can comprise inferior wall 466, posterior wall 468, side walls 470A and 470B (FIG. 10) and locking mechanism 472. The foot to which talus Tl is part of can rest against inferior wall 466. Tibia Tb can rest against posterior wall 468. Note, soft tissue not illustrated in FIGS. 10 and 11 would occupy space between lower leg and alignment boot 464. Tracking element 460 can track the location of the lower leg within surgical area 105 and tracking element 462 can track the location of alignment boot 464 within surgical area 105. Locking mechanism 472 can affix the lower let to alignment boot 464 such that the locations of the lower leg and alignment boot 464 can be correlated. As can be seen in FIG. 9, locking mechanism 472 can comprise pin 474 that can be passed through lower leg, e.g., soft tissue of the heel or the calcaneus bone, to tether the lower leg to alignment boot 464. Locking mechanism 472 can be slid on slots 476 to adjust the position of pin 474 for different sized patients, for example. Straps (not illustrated) can be passed through slots 478A and 478B (FIG. 10) in posterior wall 468 and inferior wall 466, respectively, to secure the lower leg to alignment boot 464. As such the relative position between talus Tl and tibia Tb can be fixed for performing a surgical procedure on the lower leg, such as a total ankle arthroplasty using instrument system 300. Another example of an alignment boot is disclosed in U.S. Pat. No. 10,136,952 to Couture et al., entitled "Soft Tissue Balancing in Articular Surgery," which is incorporated herein by this reference in its entirety. With the anatomy of the lower leg stabilized, oriented in a suitable position, and registered to a robotic surgical system, instrument system 300 can be used to perform a total ankle arthroplasty to implant prosthetic ankle device 60.

Figure 10:
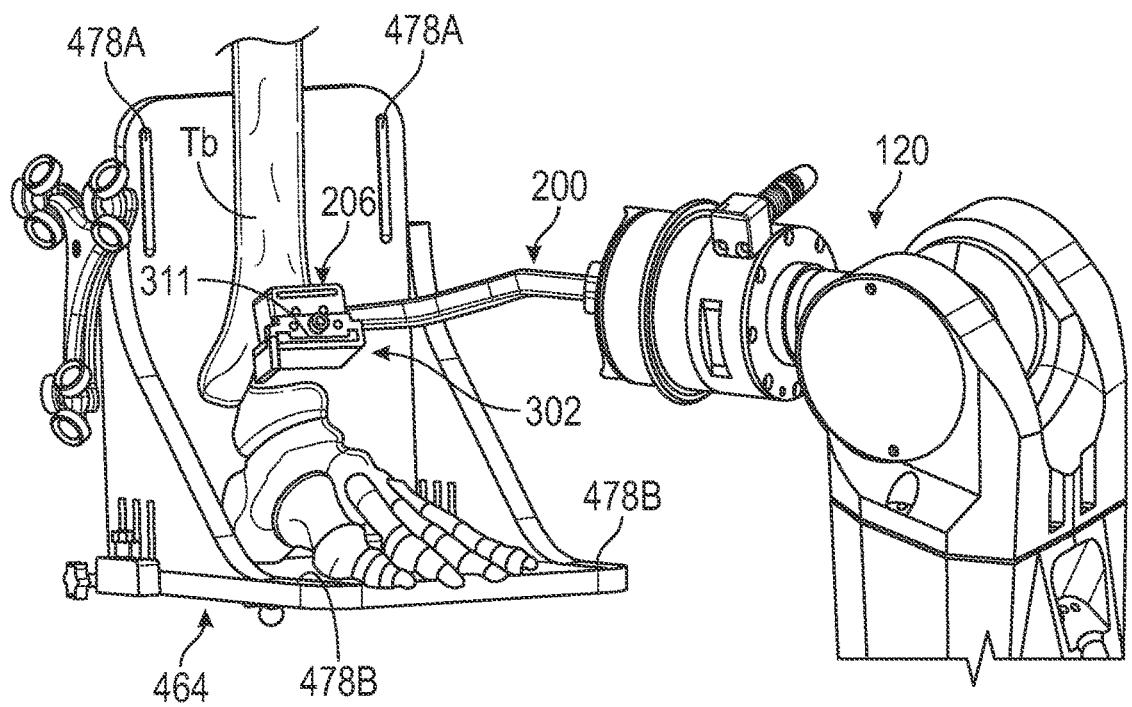
FIG. 10 is a schematic diagram of the tibia resection block positioned by a robotic arm relative to the tibia.

FIG. 10 is a schematic diagram of tibia resection block 302 positioned by robotic arm 120 relative to tibia Tb. Robotic arm 120 can position guide slot 311 of tibia resection block 302 relative to an inferior end of tibia Tb. As mentioned, pins can be inserted through bores 366A and 366B (FIG. 5A) to stabilize resection block 302.

Tibia resection block 302 can be configured in different sizes. Thus, a surgeon can be provided with a plurality of different tibia resection blocks 302, each having a different sized cutting guide slot 311. For example, a standard sized cutting block can be provided in addition to a large sized cutting block where cutting guide slot 311 is wider. The size of tibia resection block 302 selected for a specific patient can be determined pre-operatively per a surgical plan and can be based on imaging of the specific patient. The size of tibia resection block 302 can be indicated on the resection block itself. Orientation of cutting guide slot 311 can be set by robotic arm 120 based off the pre-operative surgical plan.

A cutting instrument can be inserted into cutting guide slot 311. In examples, a reciprocating or oscillating cutting or sawing blade can be slid against top surface 362 to ensure saw blade stability. Care should be taken to avoid damage postero-medially to the neurovascular bundle and centrally to the FHL tendon. Additionally, a cutting instrument can be guided along side panel 344 (FIGS. 5A-5D) to resect along the medial malleolus. Resecting of tibia Tb with cutting guide slot 311 can produce resected surfaces 480 and 482 (FIG. 14) for engagement with tibial bearing component 62 and tibial tray component 64 (FIGS. 8B and 8C).

Figure 11:
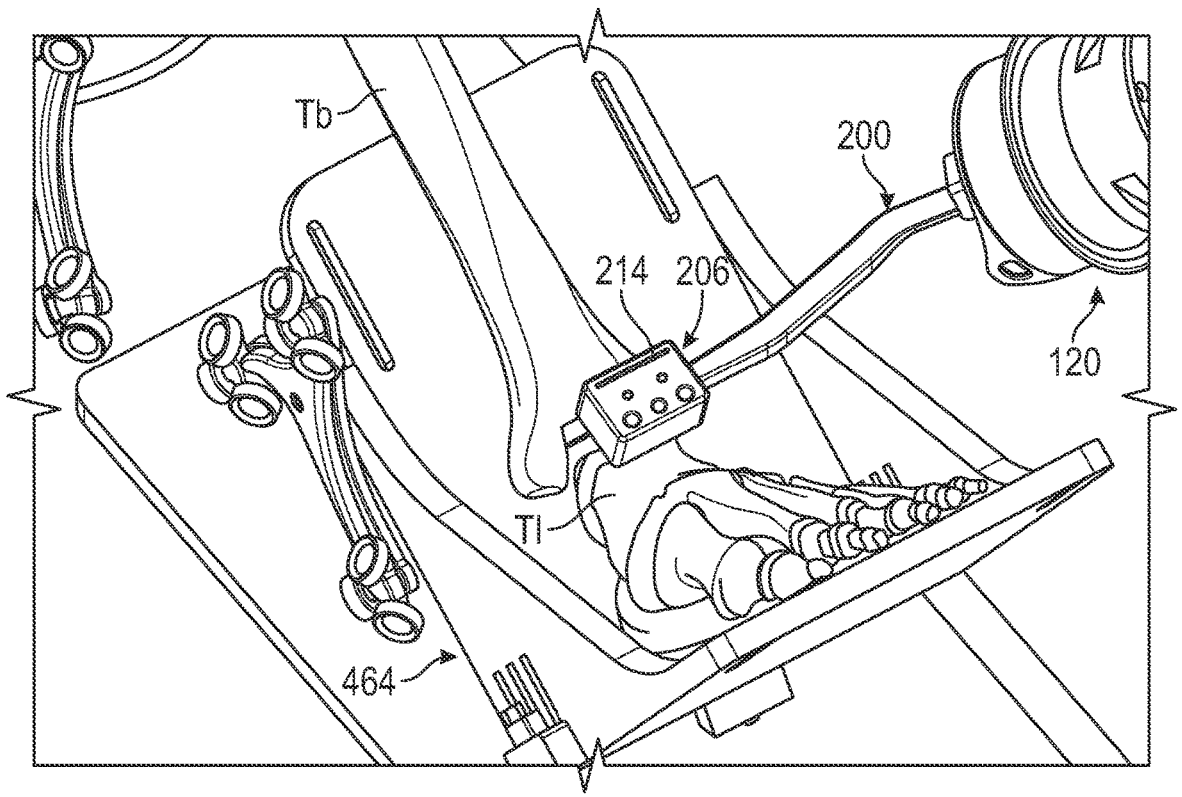
FIG. 11 is a schematic diagram of the talus resection block positioned by the robotic arm relative to the talus.

FIG. 11 is a schematic diagram of talus resection block 206 positioned by robotic arm 120 relative to talus Tl. Robotic arm 120 can position guide surface 214 of talus resection block 206 relative to a superior end of talus Tl. Orientation of guide surface 214 can be set by robotic arm 120 based off the pre-operative surgical plan. A resection blade can be inserted into guide surface 214 and operated to resect the proximal portion of talus Tl, such as via oscillatory or reciprocating motion. Care should be taken to avoid damage to neurovascular structures. As mentioned, pins can be inserted through bores 326A and 326B (FIG. 4A) to stabilize resection block 206. Resecting of talus Tl with cutting surface 214 can produce resected surface 484 (FIG. 14) for engagement with surface 87B of talus bearing component 66 (FIG. 8D).

Figure 12:
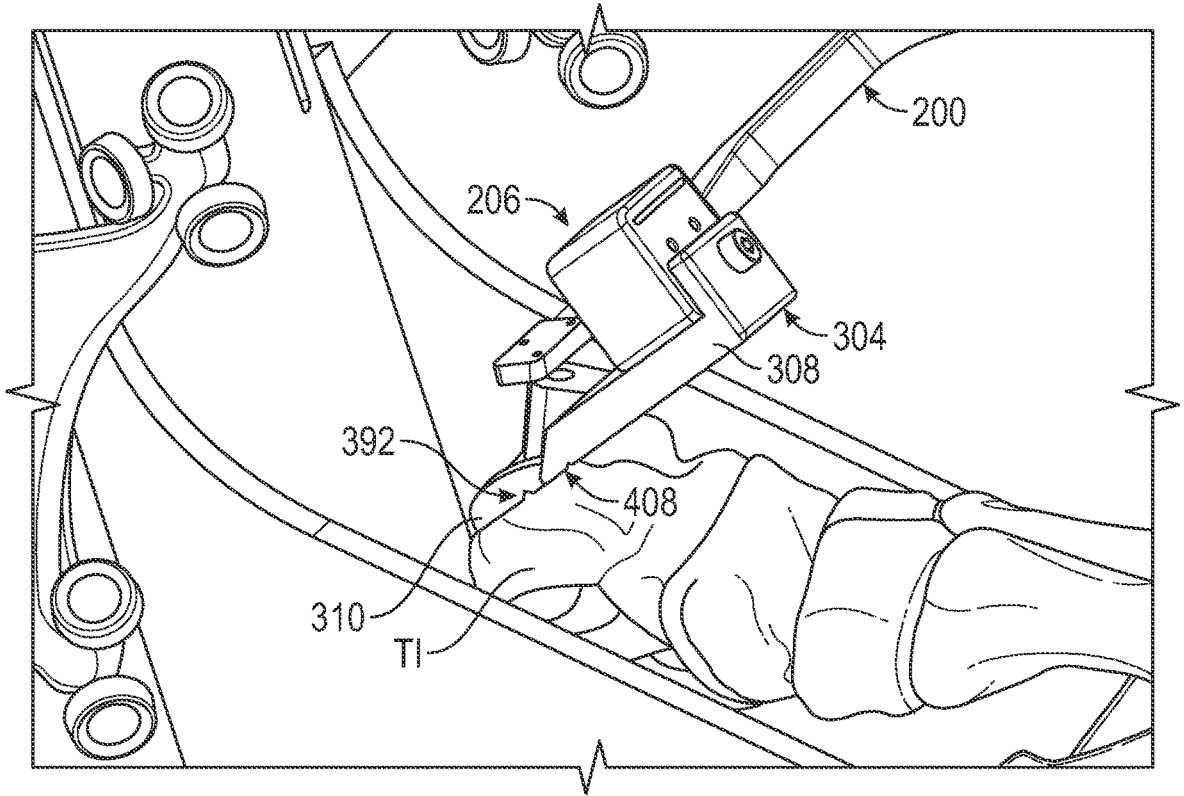
FIG. 12 is a schematic diagram of the trial implant and trial holder positioned by the robotic arm relative to the resected talus.

FIG. 12 is a schematic diagram of trial implant 310 positioned by robotic arm 120 (FIG. 11) relative to resected talus Tl. Orientation of trial implant 310 can be set by robotic arm 120 based off the pre-operative surgical plan. As mentioned, robotic arm 120 can position trial implant 310 such that a surgeon can inspect the anterior-posterior position of trial implant 310, such as be viewing the locations of alignment notches 392 and 408 against resected surface 484 (FIG. 14).

Figure 13:
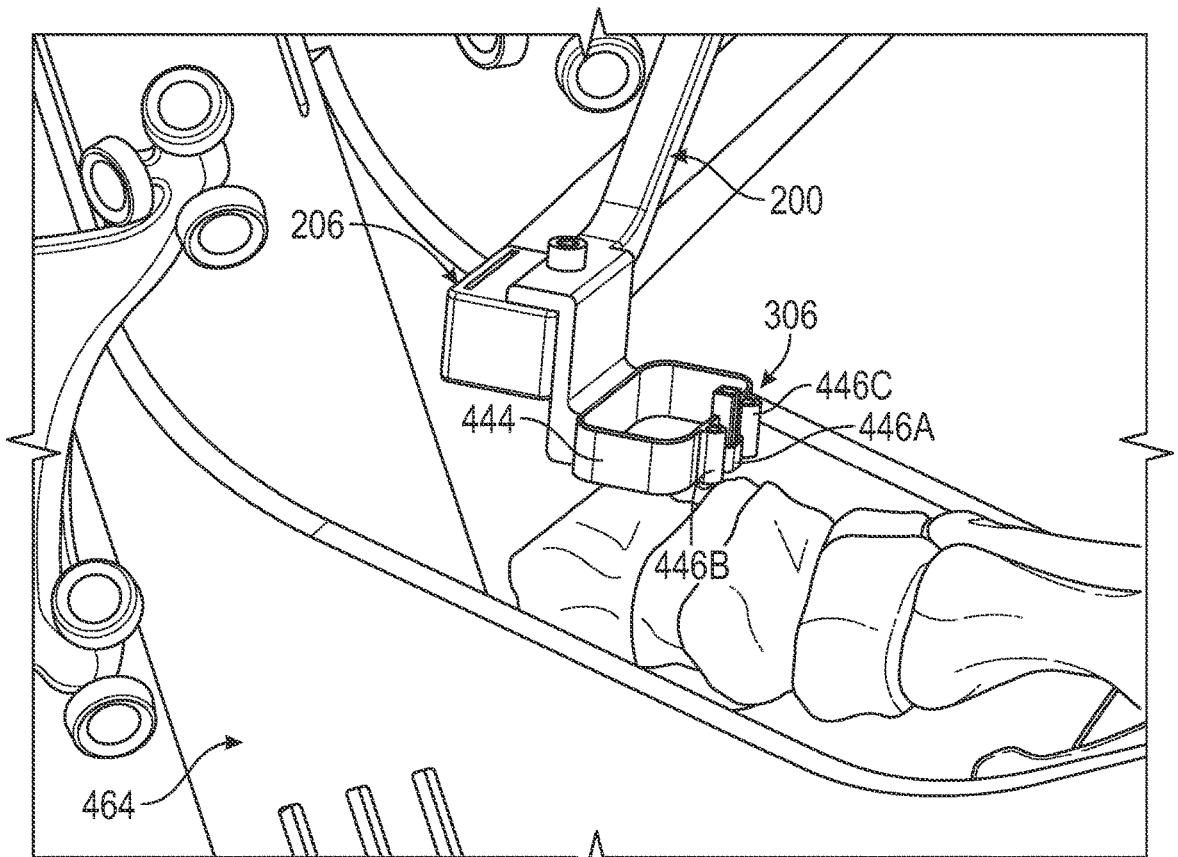
FIG. 13 is a schematic diagram of the talus reaming guide positioned by the robotic arm relative to the resected talus.

FIG. 13 is a schematic diagram of talus reaming guide 306 positioned by robotic arm 120 (FIG. 11) relative to resected talus Tl. Orientation of hoop 444 can be set by robotic arm 120 based off the pre-operative surgical plan. Reaming guide 306 can be sized appropriately for the specific patient based on bone size, according to the preoperative surgical plan. Resecting of talus Tl with hoop 444 can produce resected surface 486 (FIG. 14) for engagement with surface 87A of talus bearing component 66 (FIG. 8D).

Figure 14:
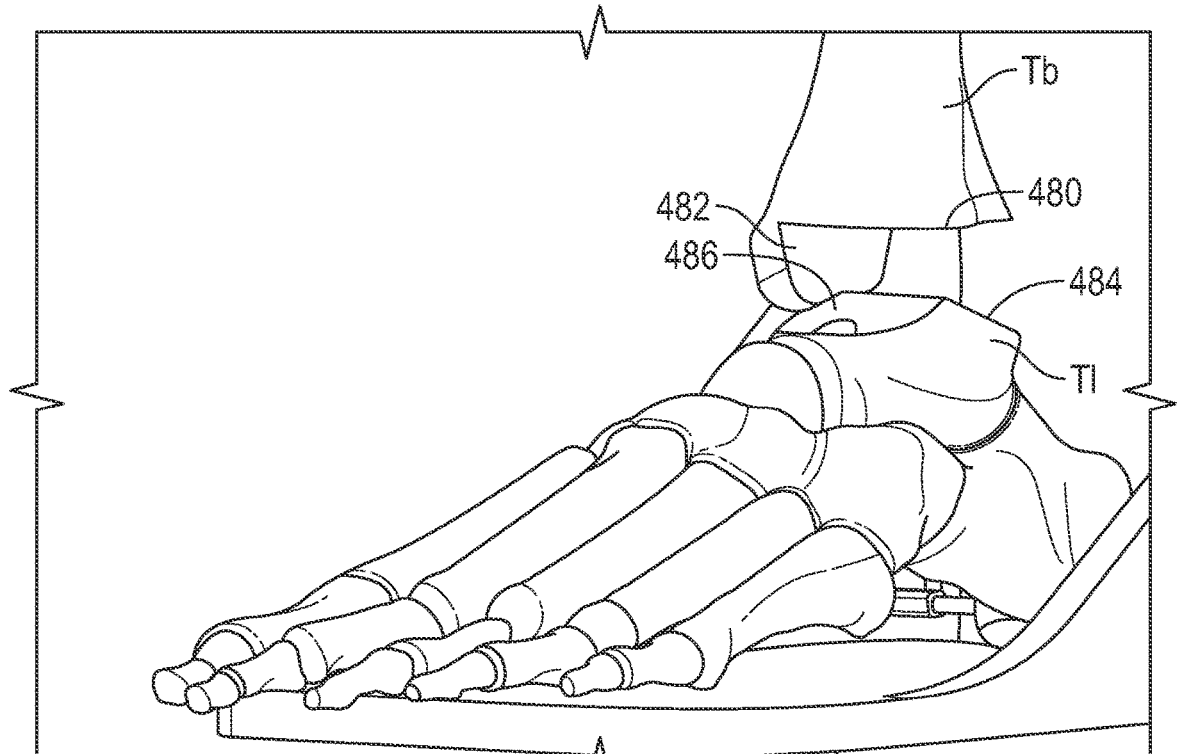
FIG. 14 is a schematic diagram of the resected tibia and the resected talus.

FIG. 14 is a schematic diagram of the resected tibia and the resected talus. Tibia Tb can be resected such that the distal end of tibia Tb and the medial malleolus are resected. The distal end is resected, such as by using cutting guide slot 311 to produce resected surface 480 and the medial malleolus is resected, such as by using side panel 344 (FIGS. 5A-5D), to produce resected surface 482. Resected surface 480 can be perpendicular to the mechanical axis of tibia Tb and resected surfaces 482 can be oblique to resected surface 480. As such, tibia Tb can be prepared to receive tibial tray component 64 (FIG. 8C). Talus Tl can be resected such that a posterior end of talus Tl is resected by talus guide block 206 (FIGS. 4A-2C) to form resected surface 484 for engaging second surface 87B (FIG. 8D) and an anterior portion of talus Tl is resected by talus reaming guide 306 (FIGS. 7A-7C) to form resected surface 486 for engaging first surface 87A (FIG. 8D).

Figure 15:
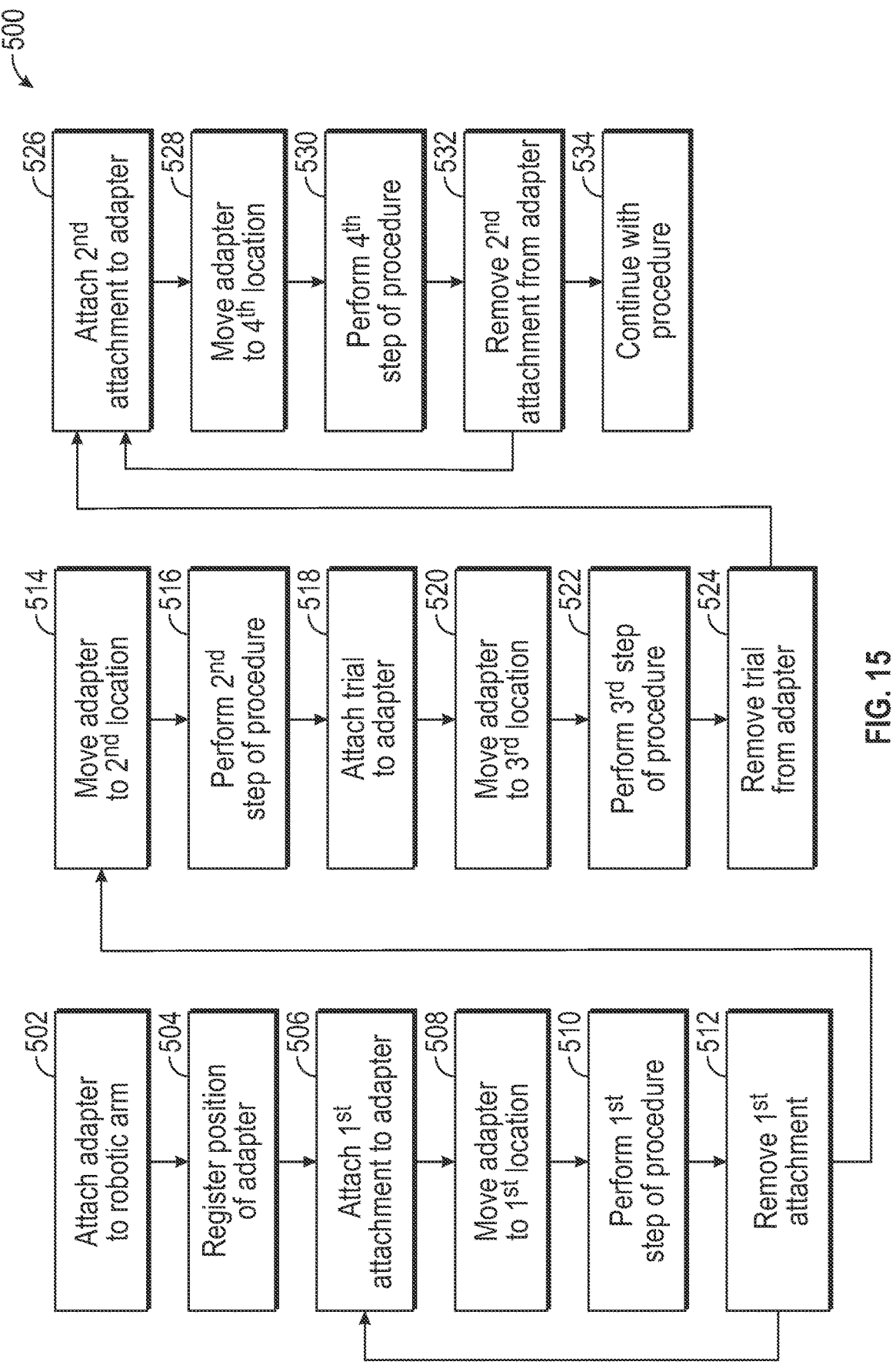
FIG. 15 is a flow chart illustrating steps of methods for performing a medical procedure, such as total ankle arthroplasty, using a universal instrument adapter and attachment instruments described herein.

FIG. 15 is a flow chart of method 500 illustrating steps 502-534 for performing a total ankle arthroplasty using universal instrument adapter 200 (FIG. 2) and surgical instrument system 300 (FIGS. 3A-3D).

At step 502, universal instrument adapter 200 can be attached to robotic arm 120.

At step 504, universal instrument adapter 200 can be registered to a coordinate system of surgical system 100. For example, the geometry and dimensions of instrument adapter 200 can be stored in memory of robotic system 115. Likewise, the geometries and dimensions of tibia resection block 302, talar trial system 304 and talus reaming guide 306 can be stored in memory of robotic system 115. In particular, for example, the relative locations between interface 216 and tool base 202 for universal instrument adapter 200, the relative location between guide surface 214 and tool base 202 for adapter block 206, the relative location between fastener 348 and cutting slot 311 for tibia resection block 302, the relative location between fastener 424 and indicator notches 392 and 408 of talar trial system 304, and the relative location between fastener 450 and guide hoop 444 of talus reaming guide 306 can be stored in memory 1704 or 1706 (FIG. 17) such that processor 1702 can determine the locations of interface 216, guide surface 214, cutting slot 311, indicator notches 392 and 408 and guide hoop 444 in the three-dimensional space of robotic system 115 (FIG. 1) via coupling to robotic arm 120 (FIG. 2) at tool base 202. As such, surgical system 100 via computing system 140 can determine the location of instrument adapter 200 within the coordinate system via coupling to robotic arm 120, as well as the locations of tibia resection block 302, talar trial system 304 and talus reaming guide 306.

At step 506, tibia resection block 302 can be attached to adapter block 206.

At step 508, robotic arm 120 can move tibia resection block 302 in position relative to tibia Tb according to a surgical plan.

At step 510, tibia Tb can be resected by inserting a cutting tool through resection slot 311 to form resected surfaces 480 and 482.

At step 512, tibia resection block 302 can be removed from adapter block 206.

At step 514, robotic arm can move adapter block 206 in position relative to talus Tl according to the surgical plan.

At step 516, talus Tl can be resected by positioning a cutting tool against guide surface 214 to form resected surface 484.

At step 518, talar trial system 304 can be attached to adapter block 206.

At step 520, talar trial system 304 can be moved to insert talar trial 310 in between resected tibia Tb and talus Tl.

At step 522, the positions of alignment notch 392 and 408 can be reviewed to determine anterior-posterior placement.

At step 524, talar trial system 310 can be removed from adapter block 206.

At step 526, talus reaming guide 306 can be attached to adapter block 206.

At step 528, robotic arm can move talus reaming guide 306 in position relative to talus Tl according to the surgical plan.

At step 530, talus Tl can be resected by positioning a cutting tool within hoop 444 to form resected surface 486.

At step 522, talus reaming guide 306 can be removed form adapter block 206.

At step 534, the total ankle arthroplasty can continue. For example, prosthetic ankle device 60 can be implanted between tibia Tb and talus Tl.

FIG. 15 is described as related to a total ankle arthroplasty. However, as mentioned above, universal instrument adapter 200 can be used to perform other types of surgical procedures on other types of anatomy. As such, the specific number and types of instruments attached to universal instrument adapter 200 can vary for different procedures. Attachment, movement and removal of attachment instruments can be repeated for as many attachment instruments are desired for a particular procedure. For example, as indicated by arrows in FIG. 15, after step 512 the method can return to step 506 to perform another surgical step with another attachment instrument, and after step 532 the method can return to step 526 to perform another surgical step with another attachment instrument.

Figure 16:
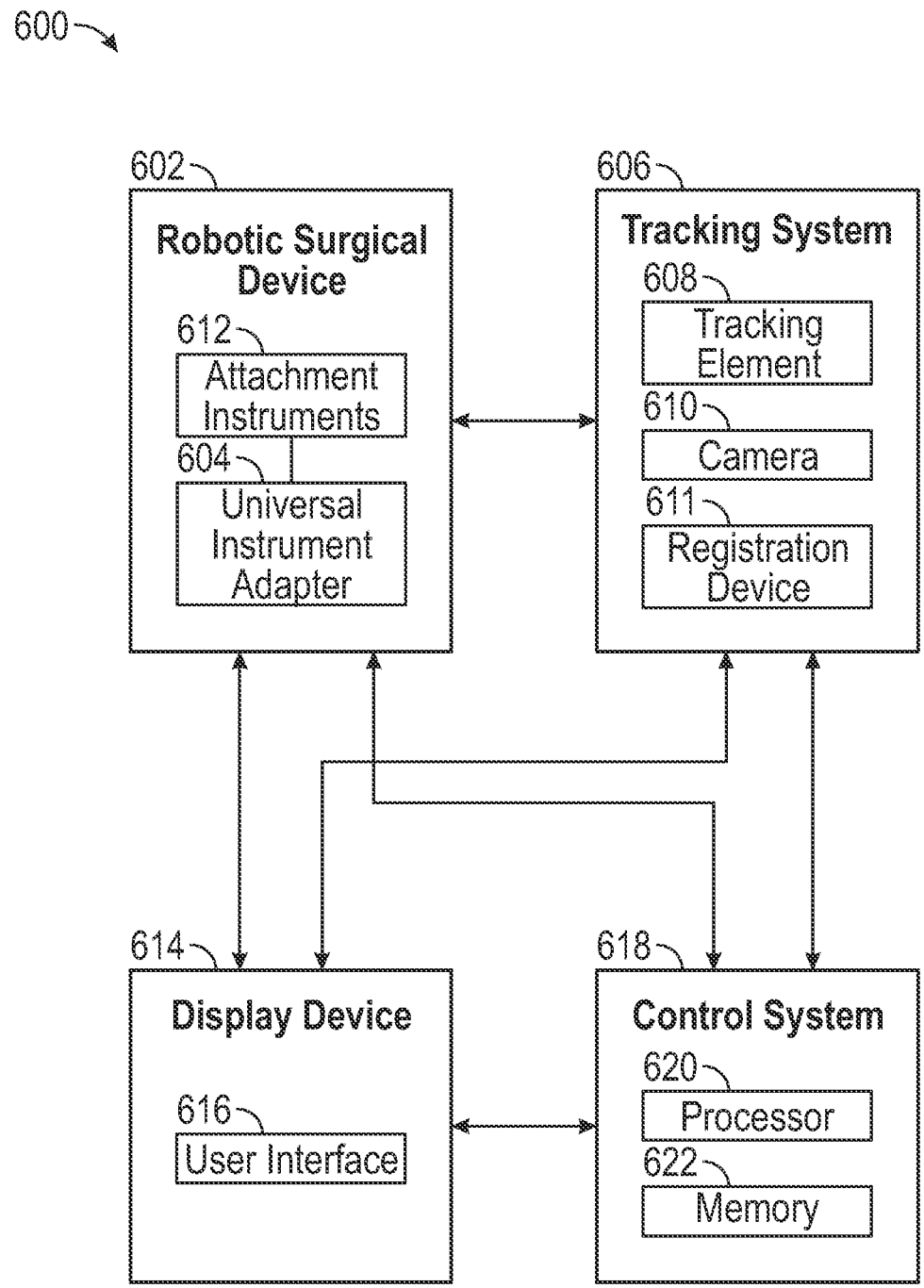
FIG. 16 is a schematic illustration of a robotic surgical system incorporating a universal instrument adapter and attachment instruments of the present application interacting with a tracking system.

FIG. 16 illustrates system 600 for performing techniques described herein, in accordance with some embodiments. System 600 is an example of a system that can incorporate surgical system 100 of FIG. 1. System 600 can include robotic surgical device 602 (e.g., robotic surgical device 115) coupled to universal instrument adapter 604 (e.g., universal instrument adapter 200 of FIG. 2), which may interact with tracking system 606. In other examples, the universal instrument adapters described herein can be used without tracking system 606. Tracking system 606 can include tracking element 608, camera 610 and registration device 611 (e.g., alignment boot 464). Instrument adapter 604 (e.g., adapter 200) can include attachment instruments 612 (e.g., tibia resection block 302, talar trial system 304 and talus reaming guide 306). System 600 can include display device 614, which can be used to display user interface 616. System 600 can include control system 618 (e.g., a robotic controller or computing system 140 of FIG. 1), including processor 620 and memory 622. In an example, display device 614 can be coupled to one or more of robotic surgical device 602, tracking system 606, or control system 618. As such, data generated by registration device 613 can be shared with control system 618, tracking system 606 and an operator of system 600 via display device 614. In examples, instrument adapter 604 can be operated without input from tracking system 608, after a registration process, such that robotic surgical device 602 can be positioned and tracked by movement of robotic arm 120 within the native coordinate system of robotic arm 120. Once in a desired position, collaborative control 612 of robotic surgical device 602 can be freely used by a surgeon without tracking system 606 required to reacquire position information for robotic surgical device and without control system 618 losing track of the location of robotic surgical device 602.

Figure 17:
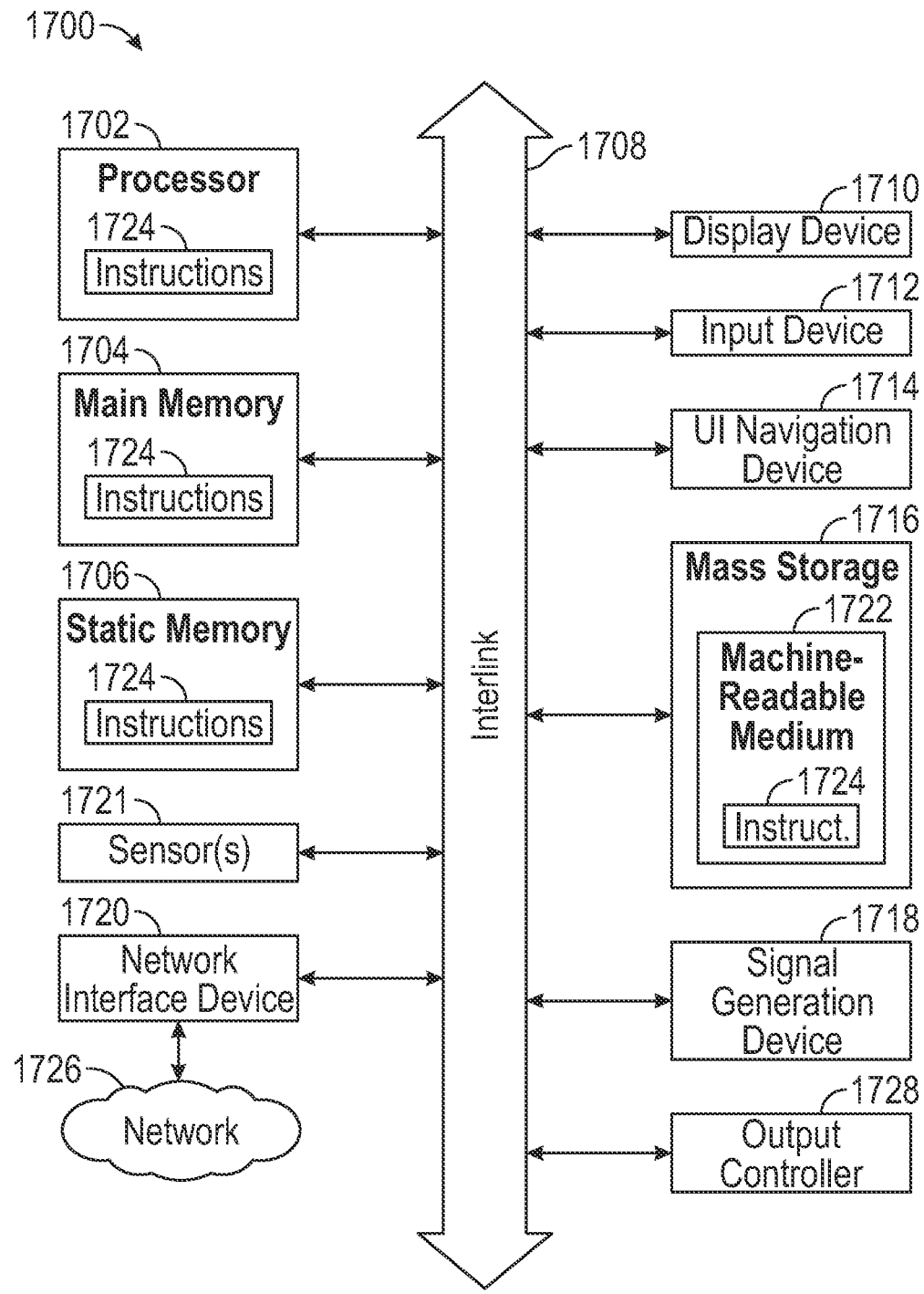
FIG. 17 is a block diagram of an example machine upon which any one or more of the techniques discussed herein may be performed and with which any of the devices discussed herein may be used in accordance with some embodiments.

FIG. 17 illustrates a block diagram of an example machine 1700 upon which any one or more of the techniques discussed herein may be performed in accordance with some embodiments. For example, machine 1700 can comprise computing system 140 of FIG. 1. Machine 1700 can comprise an example of a controller for robotic system 115 and sensors 1721 can include tracking elements 304 and 308. As such instructions 1724 can be executed by processor 1702 to generate and correlate position and orientation information to determine the position and orientation of a surgical instrument relative to robotic arm 120. For example, position information of universal instrument adapter 200 via connection to robotic arm 120 relating to the location of adapter block 206 relative to extension arm 204 can be stored in main memory 1704 and accessed by processor 1702. Processor 1702 can also receive input (such as at input device 1712) relating to the position of tibia Tb and alignment boot 464 relative to robotic arm 120 via tracking devices 460 and 462, which can be stored in main memory 1704. Processor 1702 can further relate position information of tibia resection block 302, talar trial system 304 and talus reaming guide 306 to the position information of arm 120 through universal instrument adapter 200 to correlate the position of tibia resection block 302, talar trial system 304 and talus reaming guide 306 to the coordinate system of surgical system 100. As such, as adapter block 206, and tibia resection block 302, talar trial system 304 and talus reaming guide 306 when attached thereto, moves, machine 1700 can continuously track and update the location of said components relative to robotic arm 120 via movement of robotic arm 120 and, for example, display said position on display device 1710 (e.g., user interface devices 145).

In alternative embodiments, machine 1700 may operate as a standalone device or may be connected (e.g., networked) to other machines. In a networked deployment, machine 1700 may operate in the capacity of a server machine, a client machine, or both in server-client network environments. In an example, machine 1700 may act as a peer machine in peer-to-peer (P2P) (or other distributed) network environment. Machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include hardware processor 1702 (e.g., a central processing unit (CPU), a graphics processing unit (GPU), a hardware processor core, or any combination thereof), main memory 1704 and static memory 1706, some or all of which may communicate with each other via interlink (e.g., bus) 1708. Machine 1700 may further include display unit 1710, alphanumeric input device 1712 (e.g., a keyboard), and user interface (UI) navigation device 1714 (e.g., a mouse). In an example, display unit 1710, input device 1712 and UI navigation device 1714 may be a touch screen display. Machine 1700 may additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 may include output controller 1728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 1716 may include machine readable medium 1722 on which is stored one or more sets of data structures or instructions 1724 (e.g., software) embodying or utilized by any one or more of the techniques or functions described herein. Instructions 1724 may also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 may constitute machine readable media.

While machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1724 may further be transmitted or received over communications network 1726 using a transmission medium via network interface device 1720 utilizing any one of a number of transfer protocols (e.g., frame relay, internet protocol (IP), transmission control protocol (TCP), user datagram protocol (UDP), hypertext transfer protocol (HMI, etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 1720 may include one or more physical jacks (e.g., Ethernet, coaxial, or phone jacks)

or one or more antennas to connect to communications network 1726. In an example, network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software.

The systems, devices and methods discussed in the present application can be useful in performing robotic-assisted surgical procedures that utilize robotic surgical arms that can be used to position devices relative to a patient. A universal instrument adapter can be attached to the robotic surgical arm and the dimensions of the universal instrument adapter can be stored in memory for the robotic surgical system. Likewise, the dimensions of attachment instruments that can be attached to a registered coupling point of the universal instrument adapter can be stored in memory of the robotic surgical system.

EXAMPLES

Example 1 can include or use subject matter such as a

Example 2 can include, or can optionally be combined with the subject matter of Example 1, to optionally include an Example 3 can include, or can optionally be combined with the subject matter of one or any combination of Examples 1 or 2 to optionally include Example 4 can include, or can optionally be combined with the subject matter of one or any combination of Examples 1 through 3 to optionally include a Example 5 can include, or can optionally be combined with the subject matter of one or any combination of Examples 1 through 4 to optionally include Example 6 can include, or can optionally be combined with the subject matter of one or any combination of Examples 1 through 5 to optionally include a Example 7 can include, or can optionally be combined with the subject matter of one or any combination of Examples 1 through 6 to optionally include a Example 8 can include, or can optionally be combined with the subject matter of one or any combination of Examples 1 through 7 to optionally include a Example 9 can include, or can optionally be combined with the subject matter of one or any combination of Examples 1 through 8 to optionally include Example 10 can include or use subject matter such as Example 11 can include, or can optionally be combined with the subject matter of Example 10, to optionally include a Example 12 can include, or can optionally be combined with the subject matter of one or any combination of Examples 10 or 11 to optionally include a Example 13 can include, or can optionally be combined with the subject matter of one or any combination of Examples 10 through 12 to optionally include a Example 14 can include, or can optionally be combined with the subject matter of one or any combination of Examples 10 through 13 to optionally include Example 15 can include, or can optionally be combined with the subject matter of one or any combination of Examples 10 through 14 to optionally include a Example 16 can include or use subject matter such as a method of Example 17 can include, or can optionally be combined with the subject matter of Example 16, to optionally include Example 18 can include, or can optionally be combined with the subject matter of one or any combination of Examples 16 or 17 to optionally include Example 19 can include, or can optionally be combined with the subject matter of one or any combination of Examples 16 through 18 to optionally include Example 20 can include, or can optionally be combined with the subject matter of one or any combination of Examples 16 through 19 to optionally include Each of these non-limiting examples can stand on its own, or can be combined in various permutations or combinations with one or more of the other examples.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:
1. An instrument system for performing a total ankle arthroplasty, the instrument system comprising:
    an instrument adapter comprising:
        a coupler for attaching to a robotic surgical arm;
        an extension arm extending from the coupler;
        a talus resection block attached to the extension arm, the talus resection block including a talus cutting guide surface; and
        an interface for receiving another instrument;
    a tibia resection block comprising:
        a first attachment member for coupling to the interface; and
        a tibia cutting guide surface;
    a talus reaming guide comprising:
        a second attachment member for coupling to the interface; and
        a reaming hoop for confining movement of a reamer; and
    a talar trial system comprising:
        a talar adapter for connecting to the interface; and
        a talar trial couplable to the talar adapter, the talar trial including a talar bearing surface.
2. The instrument system of claim 1, wherein the talus resection block further comprises:
    a resection body in which the talus cutting guide surface is disposed; and
    a socket defining the interface.
3. The instrument system of claim 2, wherein the talus resection block further comprises:
    first and second bores extending into the resection body, wherein the socket is disposed between the first and second bores.
4. The instrument system of claim 1, wherein the tibia resection block further comprises:
    a coupling plate including the first attachment member; and
    a resection plate extending from the coupling plate to define the tibia cutting guide surface.
5. The instrument system of claim 4, wherein the tibia resection block further comprises:
    a guide flange extending from the coupling plate and extending alongside the resection plate.
6. The instrument system of claim 1, wherein the talus reaming guide further comprises:
    a coupling plate including the second attachment member; and
    an extension plate extending from the coupling plate, wherein the reaming hoop is attached to the extension plate.
7. The instrument system of claim 1, wherein the talar adapter comprises:
    a coupling plate including a third attachment member;
    an extension plate extending from the coupling plate; and
    a coupler for connecting to the talar trial.
8. The instrument system of claim 7, wherein the talar trial comprises:
    a superior surface comprising the talar bearing surface;
    an inferior surface configured to slide along a resected talus; and
    an anterior-posterior indicator located on the inferior surface.
9. The instrument system of claim 1, wherein:
    the coupler of the instrument adapter comprises a plate; and
    the extension arm of the instrument adapter comprises:
        a first segment extending perpendicularly from the plate; and
        a second segment extending curvedly from the first segment.
10. The instrument system of claim 1, further comprising a robotic surgical system, the robotic surgical system comprising:
    a robotic arm configured to move an end of the robotic arm in relationship to a coordinate system for the robotic surgical system;
    attachment instruments, each attachment instrument having a geometry and being configured to couple with the interface, the attachment instruments comprising the tibia resection block, the talus reaming guide and the talar adapter; and
    a controller for the robotic surgical arm, the controller comprising a non-transitory storage medium having computer-readable instructions stored therein comprising:
        dimensional data for the instrument adapter;
        dimensional data for geometries of each of the attachment instruments; and
        instructions for moving the end of the robotic arm to position each of the attachment instruments into specific location within the coordinate system according to a surgical plan.
11. The instrument system of claim 10, wherein:
    the computer-readable instructions further comprise:
        location data for performing steps of a surgical procedure in the coordinate system; and
    the controller is configured to move the robotic arm to position each of the attachment instruments to perform steps of the surgical procedure.
12. The instrument system of claim 11, wherein:
    the computer-readable instructions further comprise:
        location data for the interface of the instrument adapter relative to the coupler; and location data for a fastener of each of the attachment instruments for interacting with the interface relative to an operative portion of each of the attachment instruments; and the controller is configured to determine a location of each of the operative portions relative to the end of the robotic arm.

13. The instrument system of claim 11, wherein:

the computer-readable instructions further comprise:

location data for the interface of the instrument adapter relative to the coupler; and location data for a first guide surface of a first of the attachment instruments; and the controller is configured to determine a location of the first guide surface relative to the end of the robotic arm.

14. The instrument system of claim 13, wherein:

the computer-readable instructions further comprise:

location data for a second guide surface of the instrument adapter; and the controller is configured to:

determine a location of the second guide surface relative to the end of the robotic arm; and move the second guide surface to a specific location in the coordinate system to perform a step of the surgical procedure.

* * * * *